US012758246B2

(12) United States Patent
Gagner

(10) Patent No.: US 12,758,246 B2
(45) Date of Patent: *Oct. 13, 2026

(54) MAGNETIC DEVICES FOR RESECTIONING A PORTION OF A BODILY ORGAN

(71) Applicant: GT Metabolic Solutions, Inc., Wilmington, DE (US)

(72) Inventor: Michel Gagner, Montreal (CA)

(73) Assignee: GT Metabolic Solutions, Inc., Wilmington, DE (US)

( * ) Notice: Subject to any disclaimer, the term of this patent is extended or adjusted under 35 U.S.C. 154(b) by 585 days.

This patent is subject to a terminal disclaimer.

(21) Appl. No.: 18/044,134

(22) PCT Filed: Oct. 14, 2022

(86) PCT No.: PCT/CA2022/051515

§ 371 (c)(1),
(2) Date: Mar. 6, 2023

(87) PCT Pub. No.: WO2023/060357

PCT Pub. Date: Apr. 20, 2023

(65) Prior Publication Data

US 2024/0277371 A1 Aug. 22, 2024

Related U.S. Application Data

(60) Provisional application No. 63/262,577, filed on Oct. 15, 2021.

(51) Int. Cl.
*A61B 17/32* (2006.01)
*A61B 17/00* (2006.01)

(52) U.S. Cl.
CPC ................ *A61B 17/320016* (2013.01); *A61B 17/00234* (2013.01); *A61B 2017/00269* (2013.01);
(Continued)

(58) Field of Classification Search
CPC ...... A61B 17/320016; A61B 17/00234; A61B 17/12013; A61B 2017/00269;
(Continued)

(56) References Cited

U.S. PATENT DOCUMENTS 8,591,396 B2 11/2013 Zemlok et al.
8,870,898 B2 10/2014 Beisel et al.
(Continued)

FOREIGN PATENT DOCUMENTS

CA 2932285 6/2015
WO 2009029228 A1 3/2009
(Continued)

OTHER PUBLICATIONS

International Searching Authority—International Search Report, pertaining to International Application No. PCT/CA2021/050086 dated Apr. 23, 2021, together with the Written Opinion of the International Searching Authority, 10 pages.
(Continued)

*Primary Examiner* — Brooke Labranche
(74) *Attorney, Agent, or Firm* — Merchant & Gould P.C.

(57) ABSTRACT

There is provided a resection device to remove a portion of a solid organ of a patient in the context of resection surgeries. The resection device includes a magnet assembly implantable into a body cavity of the patient, the magnet assembly including a plurality of magnet elements flexibly connected in series. The magnet assembly is configured to be positioned around a portion of an outer surface of the solid organ to magnetically attract opposite magnet elements together to compress opposite sides of the solid organ along a resection line therebetween to separate the solid organ in a resectioned portion and a remaining portion. The magnet elements can be received in a housing and have various shapes. The resection device can include additional features
(Continued)

such as a leading elongated member that can aid in the positioning of the resection device, and a trailing elongated member.

20 Claims, 21 Drawing Sheets

(52) U.S. Cl.
CPC ............... *A61B 2017/00477* (2013.01); *A61B 2017/00818* (2013.01); *A61B 2017/00876* (2013.01)

(58) Field of Classification Search
CPC ........... A61B 2017/00477; A61B 2017/00818; A61B 2017/00876; A61B 2017/32096
See application file for complete search history.

(56) References Cited

U.S. PATENT DOCUMENTS

| | | | |
|---|---|---|---|
| 2009/0062824 | A1 | 3/2009 | Berg et al. |
| 2012/0150214 | A1 | 6/2012 | Kugler et al. |
| 2013/0253550 | A1 | 9/2013 | Beisel et al. |
| 2015/0164508 | A1 | 6/2015 | Hernandez et al. |
| 2016/0022266 | A1 | 1/2016 | Lukin et al. |
| 2016/0324523 | A1 | 11/2016 | Lukin et al. |
| 2016/0324527 | A1* | 11/2016 | Thompson ....... A61B 17/00234 |
| 2018/0271531 | A1 | 9/2018 | Beisel et al. |
| 2019/0209175 | A1 | 7/2019 | Thompson et al. |
| 2019/0224029 | A1 | 7/2019 | Thompson et al. |
| 2019/0274689 | A1 | 9/2019 | Auld et al. |
| 2021/0169485 | A1 | 6/2021 | Beisel et al. |

FOREIGN PATENT DOCUMENTS

| | | | |
|---|---|---|---|
| WO | 2009029228 | A2 | 3/2009 |
| WO | 2013009886 | A1 | 1/2013 |
| WO | 2013028390 | A1 | 2/2013 |
| WO | 2013176993 | A1 | 11/2013 |
| WO | 2014204811 | A1 | 12/2014 |
| WO | 2016014644 | A1 | 1/2016 |
| WO | 2016183039 | A1 | 11/2016 |
| WO | 2018009669 | A1 | 1/2018 |

OTHER PUBLICATIONS

International Searching Authority—International Search Report, pertaining to International Application No. PCT/CA2022/051515 dated Jan. 13, 2023, together with the Written Opinion of the International Searching Authority, 9 pages.

European Patent Office—Extended European Search Report, pertaining to European Application No. 22862318.7 dated Jul. 16, 2024, 10 pages.

* cited by examiner

MAGNETIC DEVICES FOR RESECTIONING A PORTION OF A BODILY ORGAN

CROSS-REFERENCE TO RELATED APPLICATIONS

This application is the national stage entry under 35 U.S.C. § 371 of International Patent Application No. PCT/CA2022/051515 filed on Oct. 14, 2022, and claims the benefit of U.S. Provisional Patent Application No. 63/262,577 filed Oct. 15, 2021, the disclosures of which are incorporated herein by reference in their entirety.

TECHNICAL FIELD

The technical field generally relates to medical techniques for treating digestive tract conditions. In particular, the technical field relates to medical techniques for resectioning a portion of an organ of the digestive tract.

BACKGROUND

Resection surgery procedures can be used to remove a portion of tissue or part of an organ. For instance, resection surgery procedures can be used to remove tissue or a part of an organ of the digestive system, endocrine system, and/or urinary system that is diseased or damaged. Examples of resection surgery procedures that can be performed on such organs can include hepatectomies, pancreatectomies, splenectomies, adrenalectomies, nephrectomy surgeries, and pancreaticoduodenectomies.

However, these resection surgical procedures often require alteration of the organ through cutting and removing the diseased or damaged tissue, which can cause trauma to the organ being altered and lead to excessive bleeding. Such resection surgical procedures can also lead to an increased risk of infection or other complications.

Accordingly, there remain a number of challenges with respect to resection surgical procedures.

SUMMARY

Various implementations, features and aspects of the technology are described herein, including in the claims.

In accordance with an aspect, there is provided a method for resectioning a portion of a solid organ of a patient, the method comprising the steps of: inserting a magnet assembly of a resection device into a body cavity of the patient, the magnet assembly comprising a plurality of magnet elements flexibly connected in series; positioning the magnet assembly along a resection line defined around an outer surface of the solid organ such that an anterior portion of the magnet assembly and a posterior portion of the magnet assembly face each other; magnetically coupling opposing ones of the plurality of magnet elements together to compress opposite sides of the solid organ therebetween; and allowing compression of the opposite sides of the solid organ to separate the solid organ and obtain a resectioned portion and a retained portion.

In some implementations, the resection device further comprises a first end and a second end with the magnet assembly extending between the first end and the second end.

In some implementations, the magnet assembly comprises a first zone and a second zone, and inserting the magnet assembly of the resection device into the body cavity of the patient comprises inserting the first zone of the magnet assembly first followed by the second zone of the magnet assembly.

In some implementations, positioning the magnet assembly around the at least a portion of the outer surface of the solid organ and along the resection line comprises positioning the first zone of the magnet assembly on at least one of a posterior, a lateral, and an inferior side of the solid organ and positioning the second zone of the magnet assembly on at least one of an anterior, a medial, and a superior side of the solid organ.

In some implementations, each one of the plurality of magnet elements comprises a magnet-engaging side, and magnetically coupling the opposing ones of the plurality of magnet elements together comprises magnetically attracting opposing magnet-engaging sides of the plurality of magnet elements that are facing each other.

In some implementations, the magnet-engaging sides of the plurality of magnet elements of the first zone of the magnet assembly have a first zone magnetic pole, and the magnet-engaging sides of the plurality of magnet elements of the second zone of the magnet assembly have a second zone magnetic pole that is different from the first zone magnetic pole.

In some implementations, magnetically coupling the opposing ones of the plurality of magnet elements together comprises magnetically coupling the first zone magnetic pole of the magnet-engaging sides of the plurality of magnet elements of the first zone with the second zone magnetic pole of the magnet-engaging sides of the plurality of magnet elements of the second zone.

In some implementations, allowing the compression of the opposite sides of the solid organ to separate the solid organ to obtain the resectioned portion and the retained portion comprises leaving the magnet assembly along the resection line for a given period of time.

In some implementations, the given period of time ranges from about 1 week to about 7 weeks.

In some implementations, the method further comprises removing the resection device from the body cavity of the patient once the resection portion is at least partially separated from the retained portion of the solid organ.

In accordance with another aspect, there is provided a method for resectioning a portion of a solid organ of a patient, the method comprising the steps of: inserting a leading elongated member and a magnet assembly of a resection device into a body cavity of the patient, the leading elongated member extending from a leading end of the magnet assembly and the magnet assembly comprising a plurality of magnet elements flexibly connected in series; guiding the leading elongated member to position the magnet assembly around a portion of an outer surface of the solid organ such that a first portion of the magnet assembly and a second portion of the magnet assembly face each other; magnetically coupling opposing ones of the plurality of magnet elements along a resection line to compress opposite sides of the solid organ therebetween; allowing compression of the opposite sides of the solid organ to separate the solid organ and obtain a resectioned portion and a retained portion.

In some implementations, guiding the leading elongated member comprises engaging the leading elongated member with a delivery catheter and laparoscopically guiding the leading elongated member around the at least a portion of the outer surface of the solid organ.

In some implementations, the leading elongated member is configured to remain at a subcutaneous location while the opposite sides of the solid organ are compressed.

In some implementations, the resection device further comprises a trailing elongated member extending from a trailing end of the magnet assembly, the trailing elongated member being configured to remain subcutaneously or outside the patient while the opposite sides of the solid organ are compressed.

In some implementations, the method further comprises removing the resection device from the body cavity of the patient once at least a portion of the resectioned portion is separated from the retained portion.

In some implementations, removing the resection device comprises pulling on one of the leading elongated member and the trailing elongated member to extract the resection device out of the body cavity of the patient.

In accordance with another aspect, there is provided a method for resectioning a portion of a solid organ of a patient, the method comprising the steps of: inserting a magnet assembly of a resection device into a body cavity of the patient, the magnet assembly comprising: a plurality of magnet elements flexibly connected in series; and a housing comprising an organ-contacting side and being configured to receive the plurality of magnet elements therein; positioning the magnet assembly around a portion of an outer surface of the solid organ and along a resection line such that a first portion of the organ-contacting side and a second portion of the organ-contacting side face each other; magnetically coupling opposing ones of the plurality of magnet elements together to compress opposite sides of the solid organ between the first portion and the second portion of the organ-contacting side of the housing; and allowing compression of the opposite sides of the solid organ to separate the solid organ and obtain a resectioned portion and a retained portion.

In some implementations, the organ-contacting side of the housing comprises an elongated flat contact surface.

In some implementations, the housing comprises bevelled edges.

In accordance with another aspect, there is provided a method for resectioning a portion of a solid organ in a body cavity of a patient, the method comprising the steps of: inserting a magnet assembly of a resection device into a body cavity of the patient, the magnet assembly comprising: a plurality of magnet elements flexibly connected in series, each one of the plurality of magnet elements being received in a corresponding housing comprising an organ-contacting side; positioning the magnet assembly around a portion of an outer surface of the solid organ and along a resection line such that a first portion of the organ-contacting side and a second portion of the organ-contacting side face each other; magnetically coupling opposing ones of the plurality of magnet elements together to compress opposite sides of the solid organ between the first portion and the second portion of the organ-contacting side of the housing; and allowing compression of the opposite sides of the solid organ to separate the solid organ and obtain a resectioned portion and a retained portion.

In some implementations, the organ-contacting side of the housing comprises an elongated flat contact surface.

In some implementations, the housing comprises bevelled edges.

In accordance with another aspect, there is provided a resection device to resection a portion of a solid organ in a body cavity of a patient, the resection device comprising: a magnet assembly implantable into the body cavity of the patient and comprising: a plurality of magnet elements flexibly connected in series; wherein the magnet assembly is configured to be positioned against at least a portion of an outer surface of the solid organ to magnetically couple opposing ones of the plurality of magnet elements together to compress opposite sides of the solid organ therebetween along a resection line to form a resectioned portion and a retained portion over time.

In some implementations, the resection device further comprises a leading elongated member and a trailing elongated member, with the magnet assembly extending therebetween.

In some implementations, the leading elongated member is configured for engagement with a delivery catheter to guide the magnet assembly to the solid organ and around the at least a portion of the outer surface thereof.

In some implementations, each one of the plurality of magnet elements comprises a magnet-engaging side to magnetically couple opposing magnet-engaging sides of the plurality of magnet elements facing each other.

In some implementations, the magnet assembly comprises a first zone and a second zone, the magnet-engaging sides of the magnet elements of the first zone of the magnet assembly having a first zone magnetic pole, and the magnet-engaging sides of the magnet elements of the second zone of the magnet assembly having a second zone magnetic pole that is different from the first zone magnetic pole.

In some implementations, the magnet elements have a shape selected from the group consisting of an oblong shape, a stadium shape, a circular shape, a triangular shape, a rectangular shape, and an octagonal shape.

In some implementations, the magnet elements comprise bevelled edges.

In some implementations, the magnet elements comprise rounded edges.

In some implementations, the magnet-engaging side of each of the plurality of magnet elements have a smaller surface area compared to a side of each of the plurality of magnet elements located opposite the magnet-engaging side.

In some implementations, adjacent ones of the plurality of magnet elements are flexibly connected in series via a flexible connector.

In some implementations, the flexible connector comprises a flexible string.

In some implementations, the resection device is configurable between a pre-resection configuration and a resection configuration.

In some implementations, the resection device comprises a curved region.

In some implementations, an attractive force of the magnet element is determined at least in part in accordance with one of: a thickness and a composition of the solid organ.

In some implementations, an attractive force of the magnet elements is determined so as to facilitate placement and implantation of the resection device around the portion of the outer surface of the solid organ.

In some implementations, the plurality of magnet elements flexibly connected in series are provided in sufficiently close proximity to enable formation of a substantially continuous resection line.

In some implementations, the magnet elements are received in a housing.

In some implementations, each one the magnet elements is received in a corresponding housing.

In some implementations, the housing comprises bevelled edges.

In some implementations, the corresponding housing comprises bevelled edges.

In some implementations, the plurality of magnet elements in the first zone form a first enclosed shape and the plurality of magnet elements in the second zone form a second enclosed shape, the first enclosed shape being substantially similar to the second enclosed shape and corresponding to an enclosed shape.

In some implementations, the plurality of magnet elements in the first zone and the plurality of magnet elements in the second zone together form an enclosed shape.

In some implementations, the enclosed shape is selected from the group consisting of an oblong shape, a circular shape, a triangular shape, and a quadrilateral shape.

In some implementations, adjacent ones of the plurality of magnet elements forming the enclosed shape are flexibly connected in series to each other via a connector configured to retain the enclosed shape.

In some implementations, the magnet elements of the first zone and the magnet elements of the second zone are each received in a housing defining the enclosed shape.

In some implementations, the enclosed shape defines an opening extending therethrough.

In accordance with another aspect, there is provided a resection device to resection a portion of a solid organ of a patient, the resection device comprising: a leading elongated member and a trailing elongated member; and a magnet assembly extending between the leading elongated member and the trailing elongated member, the magnet assembly being implantable into a body cavity of the patient and comprising: a plurality of magnet elements flexibly connected in series; wherein the magnet assembly is configured to be positioned around a portion of an outer surface of the solid organ by guiding the leading elongated member of the resection device to magnetically couple opposing ones of plurality of magnet elements together to compress the solid organ therebetween along a resection line to form a resectioned portion and a retained portion over time.

In some implementations, the leading elongated member is a flexible leading elongated member.

In some implementations, the flexible leading elongated member comprises at least one of a flexible cord and a flexible wire.

In some implementations, the leading elongated member is configured for engagement with a delivery catheter.

In some implementations, at least one of the leading elongated member and the trailing elongated member is configured to anchor the resection device subcutaneously or outside the patient while the opposite sides of the solid organ are compressed between the opposite magnet elements.

In some implementations, the resection device is configurable between a pre-resection configuration and a resection configuration.

In some implementations, in the resection configuration, the leading elongated member and the trailing elongated member are in proximity to each other for the resection device to form one of: a partial loop and a loop.

In some implementations, the leading elongated member and the trailing elongated member comprise a continuous elongated member configured to be slidably engageable with the magnet assembly.

In accordance with another aspect, there is provided a resection device to resection a portion of a solid organ of a patient, the resection device comprising: a magnet assembly comprising: a plurality of magnet elements flexibly connected in series; a housing configured to receive the plurality of magnet elements therein and comprising an organ-contacting side; wherein the magnet assembly is configured to be positioned around a portion of an outer surface of the solid organ to magnetically couple opposite magnet elements together to compress opposite sides of the solid organ between opposing ones of the plurality of magnet elements on the organ-contacting side of the housing.

In some implementations, the organ-contacting side of the housing comprises an elongated flat contact surface.

In some implementations, the housing has a shape selected from the group consisting of an oblong shape, a stadium shape, a circular shape, a triangular shape, a rectangular shape, and an octagonal shape.

In some implementations, the housing comprises bevelled edges.

In some implementations, the housing comprises rounded edges.

In some implementations, the organ-contacting side of the housing has a smaller surface area compared to a side of the housing located opposite the organ-contacting side.

In some implementations, the magnet elements are flexibly connected in series via a flexible connector.

In some implementations, the housing comprises a plurality of housings, each one of the magnet elements being received in a corresponding one of the plurality of housings.

In some implementations, the flexible connector is provided between adjacent ones of the plurality of housings.

In some implementations, the housing comprises a connecting portion between adjacent ones of the plurality of housings to flexibly connect together adjacent magnet elements of the plurality of magnet elements.

In some implementations, the housing receiving the plurality of magnet elements therein is a single housing.

In some implementations, the flexible connector is provided within the single housing.

In some implementations, the housing comprises metal.

In some implementations, the metal comprises at least one of stainless steel, titanium, and a medical implant grade metals.

In some implementations, the housing comprises a polymer.

In some implementations, the polymer comprises at least one of silicone, Silastic™ and a medical implant grade polymers.

In some implementations, the housing defines an enclosed shape having an opening extending therethrough.

In accordance with another aspect, there is provided a resection device to resection a portion of a solid organ of a patient, the resection device comprising: a magnet assembly implantable into a body cavity of a patient and comprising: a plurality of magnet elements flexibly connected in series, each one of the magnet elements having a magnet-engaging side; a flexible housing configured to receive the plurality of magnet elements therein, the housing comprising an organ-contacting side; wherein the device is configurable in a pre-resection configuration for insertion into the body cavity and in a resection configuration for removing at least a portion of the solid organ; wherein in the pre-resection configuration, the magnet-engaging sides of the magnet elements are magnetically uncoupled to each other, and in the resection configuration, the magnet assembly forms a U-shape around the solid organ to magnetically couple opposing ones of the magnet-engaging sides and compress opposite sides of the outer surface of the solid organ between opposing sides sections of the housing.

In some implementations, the pre-resection configuration comprises an extended pre-resection configuration.

In some implementations, the pre-resection configuration comprises a looped pre-resection configuration.

DETAILED DESCRIPTION

Figure 1:
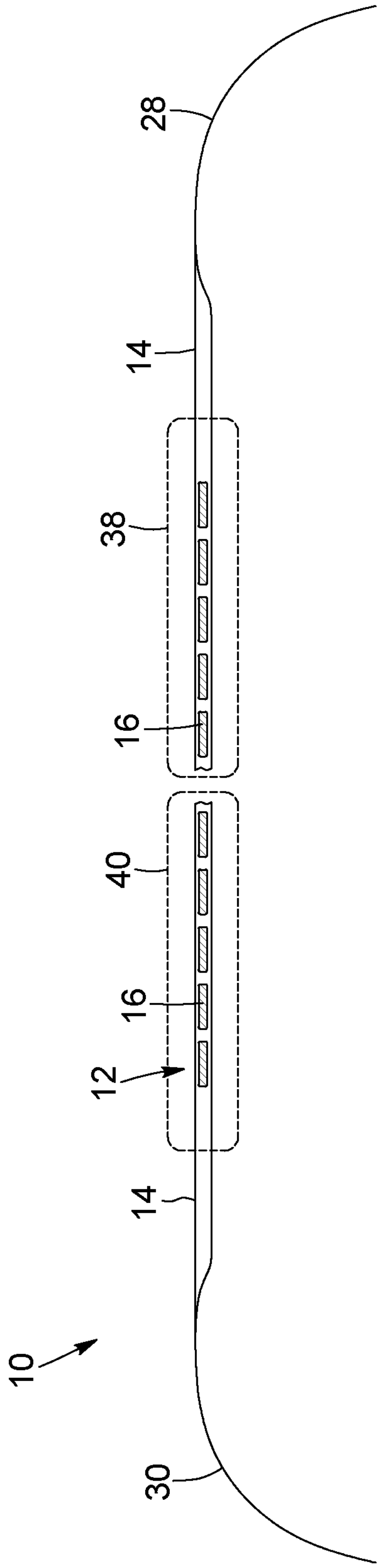
FIG. 1 is a side cross-sectional view schematic of a portion of a resection device that includes a magnet assembly having a first zone and a second zone, the resection device being shown in an extended pre-resection configuration.

Surgical procedures to treat various medical conditions associated with the digestive system, endocrine system, and/or urinary system can include modifying the configuration of an organ, such as the liver, pancreas, spleen, or kidney. In the context of the present description, reference to an organ can also include glands, such as the adrenal gland. Furthermore, it is to be understood that when referring to an "organ" herein, the term means an organ that does not include a lumen, i.e., that is not hollow, which can also be referred to as a "solid organ". Such surgical procedures can be performed for any surgery related to the digestive, endocrine, or urinary system, which can include resection surgeries, such as hepatectomies, pancreatectomies, splenectomies, adrenalectomies, nephrectomies, pancreaticoduodenectomies or other surgeries, such as those performed in the context of a cancer or tumour treatments, organ tears or lacerations, etc.

Modifying the configuration or reducing the size of a solid organ can include compressing opposing outer surfaces of the organ toward each other along a resection line over a period of time to subject a portion of the organ along the resection line to ischemic pressure necrosis, thereby facilitating resection of a portion of the organ without cutting or transecting the organ at the time of the initial surgery, and reducing bleeding risks. In order to do so, a method for resectioning a portion of a solid organ progressively over time can be implemented using a resection device as described herein. The resection device may include various features. It is to be understood that as used herein, the expression "resection device" can be used interchangeably with the expression "resection implant" throughout the present description, as the resection device is configured to be implanted and remain a certain period of time, which can extend from days to weeks, within a body cavity of the patient, such as a ventral body cavity including the thoracic cavity, abdominal cavity and pelvic cavity.

The resection device can include a flexible magnet assembly that can be inserted into the body cavity of the patient and positioned around a portion of the outer surface of a target solid organ. The flexibility of the magnet assembly can be conferred by flexibly connecting a series of magnet elements together to form a train of magnet elements. Each one of the magnet elements includes a respective magnet-engaging side, and consecutive ones of magnet elements have their respective magnet-engaging side on the same side. In some implementations, one or more magnet elements can be received in a respective housing, or the series of magnet elements can be received together in a single housing.

The resection device can be configured to adopt a pre-resection configuration and a resection configuration. The pre-resection configuration can facilitate the insertion of the resection device into the body cavity of a patient, for instance in the context of a laparoscopy procedure, and subsequent placement around a target solid organ. On the other hand, the resection configuration is a configuration that can enable resectioning of a portion of the solid organ.

In the pre-resection configuration, the magnet-engaging sides of the plurality of magnets are magnetically uncoupled to each other. To achieve such a pre-resection configuration, the magnet assembly can extend longitudinally such that the magnet-engaging sides are not facing each other and can be inserted into the body cavity longitudinally, e.g., as a string. This type of pre-resection configuration can be referred to as an extended pre-resection configuration. In another example of pre-resection configuration, the magnet assembly can form a U-shape to obtain a partial or closed loop with opposite magnet-engaging sides of the magnet elements facing each other, but being far enough from each other that the opposite magnet-engaging sides of the magnet elements remain magnetically uncoupled so as to allow the partial or closed loop to be placed around a target solid organ. This pre-resection configuration can be referred to as a looped pre-resection configuration.

The choice of pre-resection configuration can depend on the target solid organ around which the magnet assembly will be placed, and can take into consideration the space available around the target solid organ. If the magnet assembly is initially inserted as a string, the pre-configuration will eventually include the formation of the U-shape for placement around the target solid organ while the magnet elements remain magnetically uncoupled. In addition to facilitating the insertion of the resection device into the body cavity, the pre-resection configuration can facilitate placement of the magnet assembly around the outer surface of the target solid organ along a given resection line. In the context of the present description, the resection line corresponds to a demarcation between two portions of a target solid organ, a resectioned portion corresponding to the portion being removed from the solid organ, and a retained portion corresponding to the portion of the solid organ that remains intact in the patient. Thus, the resection line corresponds to a tracing where the magnet-engaging sides of the magnet assembly are placed against to resection the target solid organ.

Once the resection device is placed around the outer surface of the target solid organ, the magnet assembly can be placed in the resection configuration along the resection line. In the resection configuration, opposite magnet elements on each side of the target solid organ and close to the outer periphery of the target solid organ are placed in sufficiently close proximity so that opposite magnet-engaging sides of the magnet elements facing each other are magnetically coupled to each other to compress the portion of target solid organ that is between the magnetically coupled magnet elements, leading to ischemic pressure necrosis of that portion of the target solid organ and bringing closer together the magnetically coupled magnet elements. Over time, magnet elements further away from the outer periphery of the target solid organ and thus closer to a center region of the target solid organ become magnetically coupled as well, such that eventually, all magnet elements along the resection line are magnetically coupled to each other. Thus, the magnetic attraction maintains the magnet elements in place, and the pressure applied by the magnet elements on the target solid organ along the resection line compresses the organ to restrict blood flow to the target solid organ, first along the outer edges of the target solid organ, which can be thinner than a central portion thereof, and then progressively toward the central portion of the target solid organ, resulting in a progressive transection of the organ that occurs over time. A progressive transection allows the organ's healing mechanism to gradually heal the necrotic tissue along the edges of the magnet elements, eventually allowing the subsequent resection of the organ along the resection line.

In some implementations, the magnet elements can be provided in a continuous formation that defines an enclosed shape that, when positioned along an enclosed resection line on the central portion of the organ or an area near the periphery of the organ, couple to magnet elements also provided in a continuous formation on an opposing side of the organ. The magnet elements forming an enclosed shape on opposing sides of the target solid organ can magnetically couple to each other, such that the pressure applied by the magnet elements along the resection line compresses the organ to restrict blood flow to the enclosed portion inside the enclosed resection line or the area along the periphery of the organ, resulting in a progressive carving out of the resectioned portion, either in the interior of the organ or along the periphery of the organ.

In the context of the present description, the term "resection" or "resectioning" can be interpreted as corresponding to a process that involves separating a portion of a solid organ, the portion to be separated being the "resectioned" portion, from a remaining portion of the solid organ, the portion remaining in the body cavity being the "retained portion". When using the terms "separation" or "separate", it is to be understood that the separation can include the creation of a demarcation corresponding substantially to the width of the magnet elements between the resectioned portion and the retained portion, without the resectioned portion and the retained portion being physically separated from each other. In such implementations, which can also be referred to as a partial resection, the resectioned portion and the retained portion can be connected with loose or areolar connective tissue or scar tissue. Alternatively, the terms "separation" or "separate" can include a physical separation of the resectioned portion from the retained portion, which can also be referred to as a complete resection. The term "transection" refers to a division of the solid organ transversely, into distinct portions and can include a transverse division between the resectioned portion and the retained portion where the portions are partially connected, such as with loose or areolar connective tissue or scar tissue. In the context of a transection using the magnetic device as described herein, such transection can be achieved by progressive ischemic pressure necrosis occurring due to the compression of the organ along the resection line. After a certain period of time, which can extend from days to weeks, the solid organ can be physically separated into two distinct portions, i.e., the resectioned portion that can be removed from the body cavity of the patient, and the retained portion that remains in the body cavity of the patient. Alternatively, the distinct resectioned portion and retained portion of the solid organ can be partially attached to each other, for example, with 1 to 3 mm of loose or areolar connective tissue or scar tissue.

The resection device is configured to remain in the body cavity of the patient for a period of time that is sufficient to allow the magnet elements to couple to each other and allow the healing process to take place around the magnet elements following the ischemic pressure necrosis of the organ along the resection line. During the healing process, a fibrous capsule can form around the magnet elements. During removal of the resection device, the fibrous capsule can be surgically divided to remove the resection device and the resectioned portion of the solid organ. Monitoring of the healing process can be advantageous to determine at which moment it may be advisable to remove the resection device and the resectioned portion out of the body cavity of the patient after the necrosis of the tissue in the retained portion has occurred. Monitoring of the relative position of the resection device, for example by regular X-rays, can enable determining when the opposing magnet elements are coupled and thus determine at which moment it may be advisable to remove the resection device and the resectioned portion of the organ from the body cavity.

The resection device can also include additional features. For instance, the resection device can include one or more features that can contribute to aid in the placement of the magnet assembly within the body cavity. Such features can include a flexible elongated member, such as a flexible cord or a flexible wire, that is configured to extend from one extremity of the magnet assembly and that can also be referred to as leading elongated member. The flexible elongated member can be configured for engagement with a delivery catheter, and in turn, the delivery catheter can be used to carry and navigate the magnet assembly via the leading elongated member into the body cavity, and around the target solid organ.

Optionally, the resection device can also include a second flexible elongated member at the other extremity of the magnet assembly, opposite the leading elongated member, and this second flexible elongated member can be referred to as trailing elongated member. The trailing elongated member can be useful during implantation of the magnet assembly if a contact with the magnet assembly from outside of the patient is desired. Either one of the leading elongated member and the trailing elongated member, or both of them, can also be useful to anchor the resection device subcutaneously or outside the patient during the healing period.

Various implementations of the resection device and associated methods will now be described in greater detail.

Magnet Assembly

Magnet Elements

Figure 2:
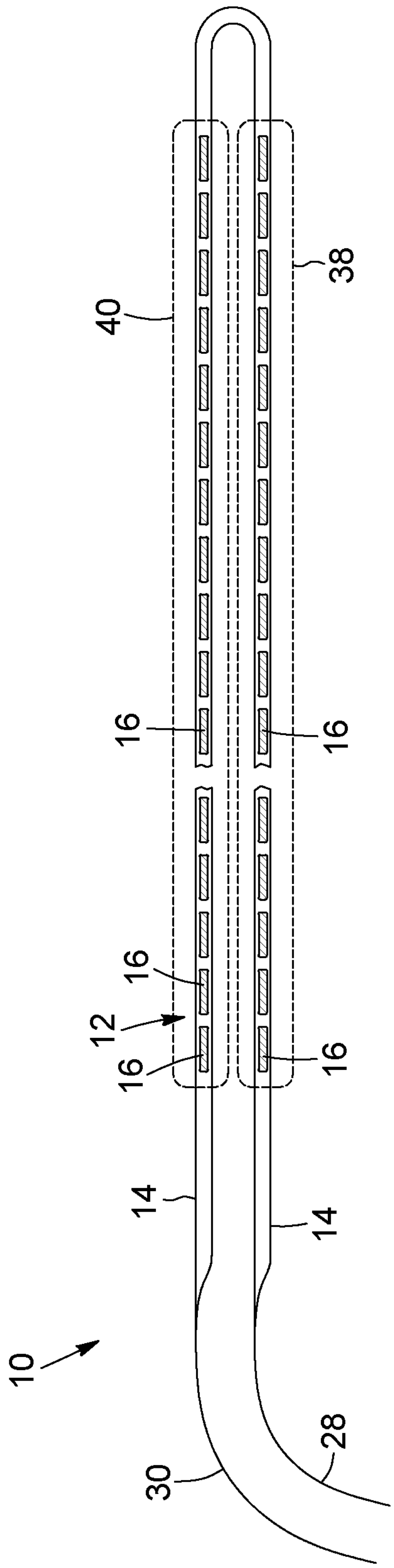
FIG. 2 is a side cross-sectional view schematic of a portion of a resection device that includes a magnet assembly having a first zone and a second zone, the resection device being shown in a looped pre-resection configuration.
Figure 3:
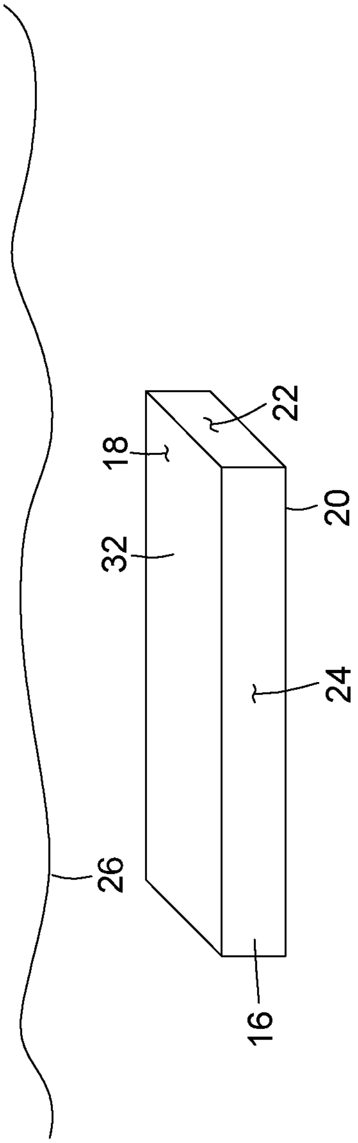
FIG. 3 is a perspective view schematic of a magnet element in an arbitrary spatial relationship with an outer surface of a portion of a solid organ.

With reference to FIGS. 1 to 3, an implementation of a resection device 10 is shown. The resection device 10 includes a magnet assembly 12 that is received in a housing 14. The magnet assembly 12 includes a plurality of magnet elements 16 that are connected or joined together in a flexible manner. The magnet element 16 includes a top side 18, a bottom side 20, lateral sides 22 and longitudinal sides 24. In the context of the present description, the top side 18 of the magnet element 16 refers to the side that faces the outer surface 26 of the target solid organ once the magnet assembly 12 is implanted in the patient and placed around the outer surface of the target solid organ. In the implementation shown, the resection device 10 further includes a flexible elongated member at each extremity, i.e., a leading elongated member 28 and a trailing elongated member 30. In addition, the housing 14 in which the magnet elements 16 are received is also flexible.

In FIG. 1, the resection device 10 is in a pre-resection configuration, where the resection device 10 is extended longitudinally such that the extremities of the magnet assembly 12 are spaced apart and opposite to each other. This type of pre-resection configuration can be referred to as an extended pre-resection configuration. In FIG. 2, the resection device 10 is also in a pre-resection configuration, albeit one that can be referred to as a looped pre-resection configuration. In the looped pre-resection configuration, the magnet assembly 12 is folded on itself in a U-shape to form a partial or closed loop, depending on the intended application. The choice of the pre-resection configuration for the magnet assembly 12 can depend on the solid organ that is targeted to treat, and the choice of insertion method that is considered. As mentioned above, if the magnet assembly 12 is initially inserted as a string such as in shown in FIG. 1, the pre-resection configuration eventually includes the formation of the U-shape in a partial or closed loop for placement around the target solid organ while the magnet elements 16 remain magnetically uncoupled. In other words, one of the characteristics of the pre-resection configuration of the magnet assembly 12 is that the magnet elements 16 are magnetically uncoupled, and in the pre-resection configuration, the magnet assembly 12 can adopt various configurations where the magnet elements 16 are magnetically uncoupled. In addition to facilitating the insertion of the resection device 10 into the body cavity, the pre-resection configuration can also facilitate placement of the magnet assembly 12 around the outer surface of the target solid organ along a given resection line 42. Additional details regarding these considerations are provided below.

The magnet elements 16 of the magnet assembly 12 can be any type of suitable magnet. In some implementations, the magnet elements 16 can be chosen according to their attractive force, i.e., according to the pressure that will be exerted on the surface area of the tissue of the solid organ that will eventually be compressed between magnetically coupled magnet elements 16. Factors influencing the attractive force of the magnet element 16 can include the shape of the magnet element 16, the thickness of the magnet element 16, the material that the magnet element 16 is made of, etc. Examples of materials can include neodymium magnets (e.g., NdFeB magnets), rare earth magnets and ferrite magnets.

Figure 4:
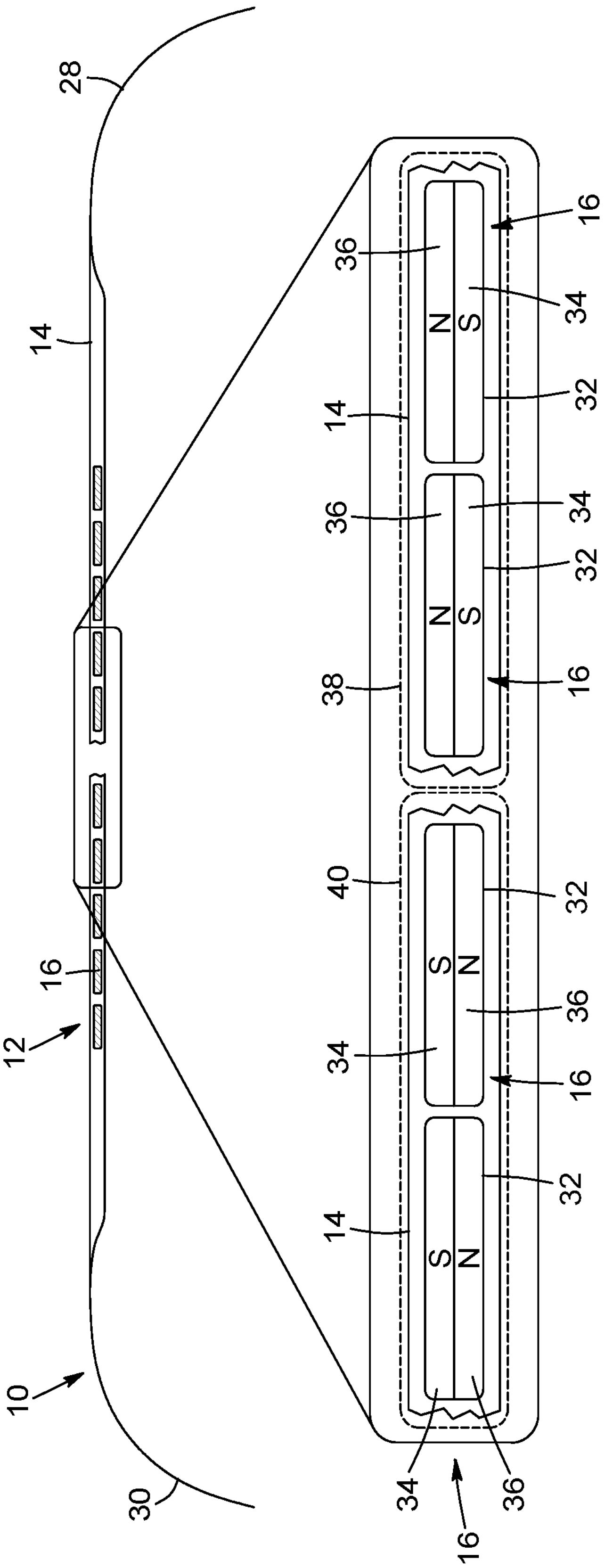
FIG. 4 is a side cross-sectional view schematic of a resection device in an extended pre-resection configuration, with an enlarged view of magnet elements in a first zone of a magnet assembly and magnet elements in a second zone of the magnet assembly.
Figure 5:
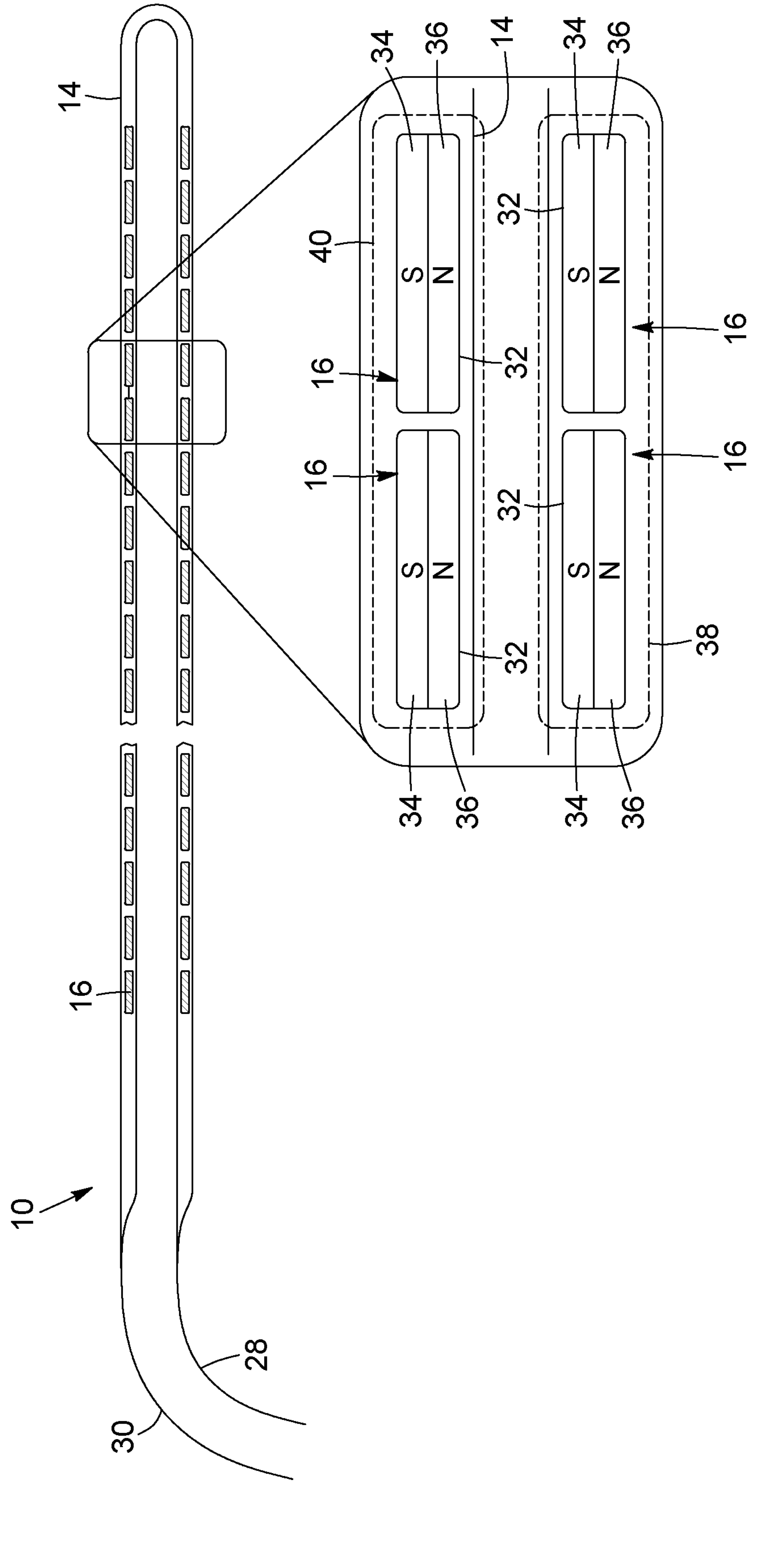
FIG. 5 is a side cross-sectional view schematic of a resection device in a looped pre-resection configuration, with an enlarged view of magnet elements in a first zone of a magnet assembly and magnet elements in a second zone of the magnet assembly.

With reference now to FIGS. 4 and 5, each one of the magnet elements 16 can be a dipole magnet having magnetic poles across the thickness of the magnet element 16, such that the magnet element 16 includes a first magnetic pole 34 on one side thereof and a second magnetic pole 36 on another side thereof, the second magnetic pole 36 being different than the first magnetic pole 34. One side of the magnet element 16 corresponds to a magnet-coupling side 32, which is the side of the magnet element 16 that will eventually face the tissue or outer surface 26 of the solid organ to be treated once the magnet assembly 12 is installed around the outer surface of the target solid organ, which is also referred to above as the top side 18 of the magnet element 16.

Figure 7:
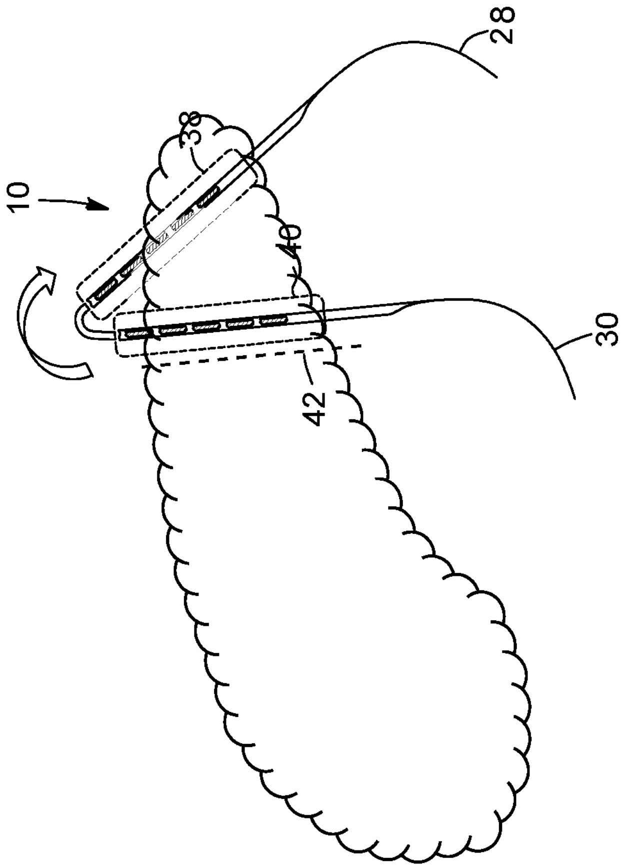
FIG. 7 is a top cross-sectional view schematic of the resection device shown in FIG. 6 and being folded around the outer surface of the pancreas to be placed in a looped pre-resection configuration.
Figure 6:
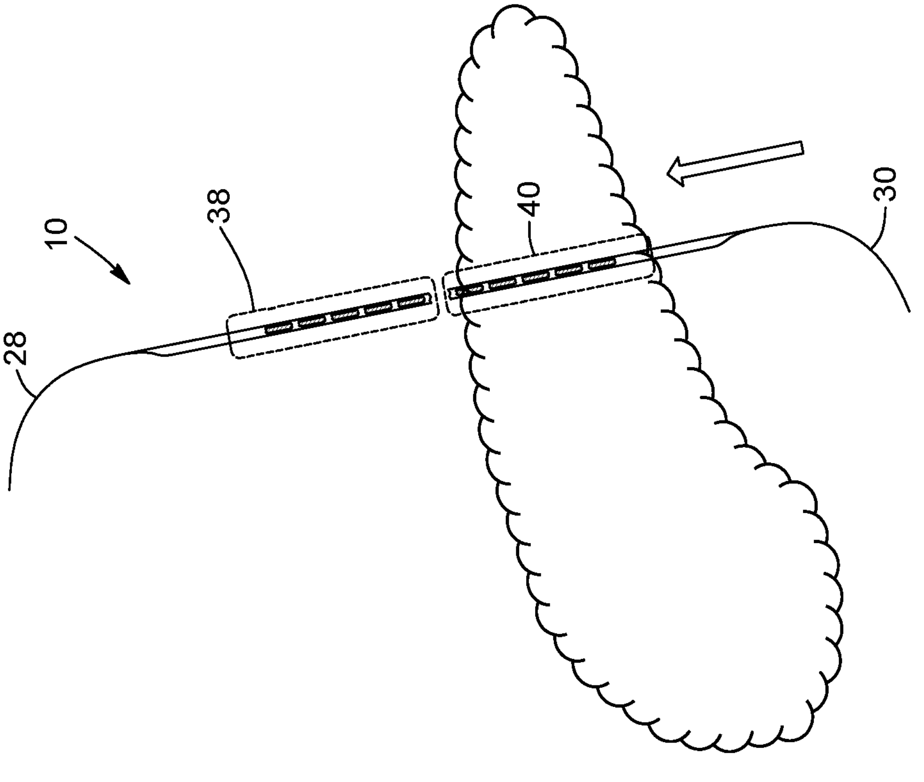
FIG. 6 is a top cross-sectional view schematic of a resection device in an extended pre-resection configuration shown for subsequent placement around an outer surface of a pancreas.

The magnet elements 16 are positioned strategically along the length of the magnet assembly 12 to obtain a desired functionality of the magnet assembly 12. With reference to FIGS. 1 to 10, a first zone 38 and a second zone 40 of the magnet assembly 12 are represented. The first zone 38 of the magnet assembly 12 corresponds to a portion of the magnet assembly 12 that would be the first to be inserted into the body cavity of the patient, when the resection device 10 is in an extended pre-resection configuration such as in FIG. 1, by guiding the leading elongated member 28 into the body cavity, such as in FIG. 6. Then, the first zone 38 of the magnet assembly 12 would be the one that is flipped around the outer surface of the target solid organ in a second position (in the case of FIG. 7, in a posterior position), such as shown in FIG. 7. The second zone 40 corresponds to a portion of the magnet assembly 12 that follows the first zone 38 when the magnet assembly 12 is inserted into the body cavity, and then that remains in a first position (in this case of FIG. 7, in an anterior position) without being flipped around the outer surface of the target solid organ, such as shown in FIG. 7.

Figure 10:
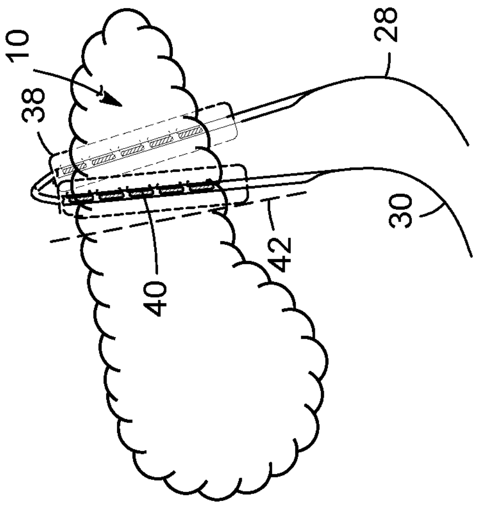
FIG. 10 is a top cross-sectional view schematic of the resection device shown in FIG. 9 and placed around the outer surface of the pancreas in the looped pre-resection configuration.
Figure 9:
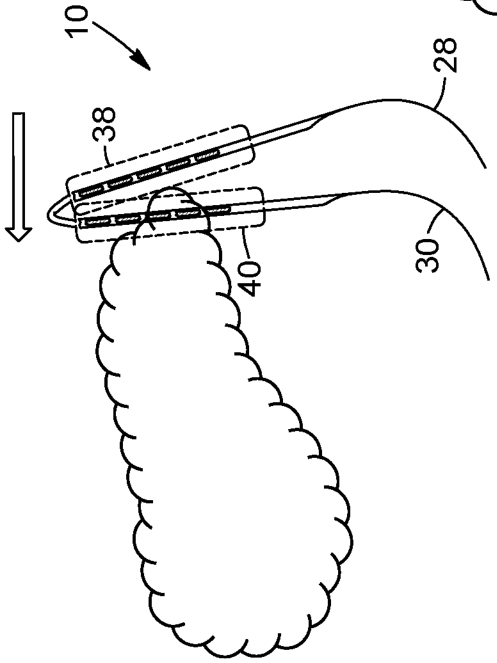
FIG. 9 is a top cross-sectional view schematic of the resection device shown in FIG. 8 and being translated for placement around the outer surface of the pancreas.
Figure 8:
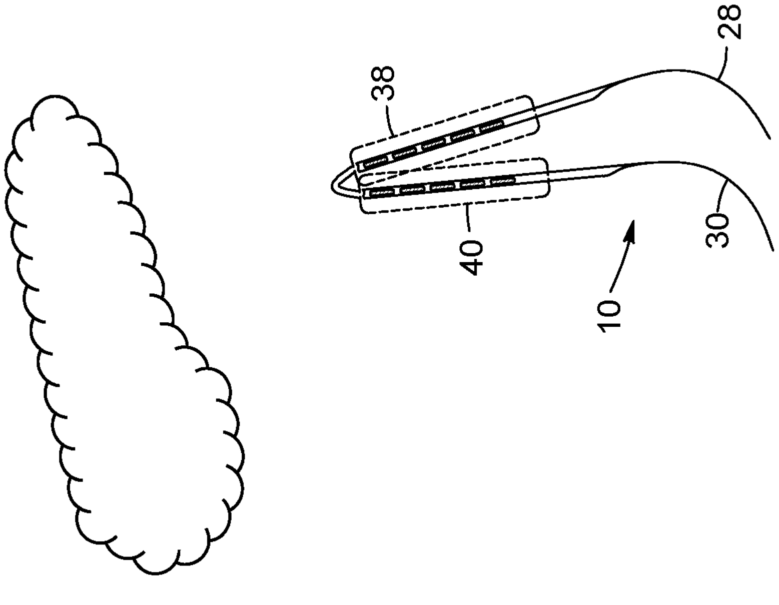
FIG. 8 is a top cross-sectional view schematic of a resection device in a looped pre-resection configuration shown for subsequent placement around an outer surface of the pancreas.

Referring to FIGS. 8 to 10, in implementations where the magnet assembly 12 is already in a looped pre-resection configuration, the first and second zone 38, 40 of the magnet assembly 12 can be navigated in the body cavity side-by-side rather than being extended. In such implementations, the first zone 38 of the magnet assembly 12 can be said to correspond to a portion of the magnet assembly 12 that would be in a second position (in the case of FIGS. 8 to 10, in a posterior position) once inserted in the body cavity of the patient, and the second zone 40 can be said to correspond to a portion of the magnet assembly 12 that would be in a first position (in the case of FIGS. 8 to 10, in an anterior position) once inserted in the body cavity of the patient, or vice-versa.

Referring back to FIGS. 4 and 5, the first zone 38 includes a series of magnet elements 16 that each has a magnet-coupling side 32 having a same magnetic pole among each other (i.e., a first zone magnetic pole), and the second zone 40 includes a series of magnet elements 16 that also each have a magnet-coupling side 32 having a same magnetic pole among each other (i.e., a second zone magnetic pole), but that is different from the magnetic pole of the magnet-coupling side 32 of the magnet elements 16 of the first zone 38. The magnet-coupling side 32 corresponds to the top side 18 of the magnet element 16 described above, i.e., the side that faces the outer surface of the solid organ. For instance, as shown in FIG. 4, the resection device 10 is in an extended pre-resection configuration, and the second zone 40 of the magnet assembly 12 is longitudinally spaced apart from the first zone 38. The magnet-coupling side 32 of the magnet elements 16 of the first zone 38 has a North pole, and the magnet-coupling side 32 of the magnet elements 16 of the second zone 40 has a South pole. Similarly, in FIG. 5, the resection device 10 is in a looped pre-resection configuration, and the magnet-coupling side 32 of the magnet elements 16 of the first zone 38 has a North pole, and the magnet-coupling side 32 of the magnet elements 16 of the second zone 40 has a South pole.

This configuration of the magnet assembly 12, with the magnet elements 16 having a different magnet-coupling side 32 depending on the zone 38, 40 that they are in along the magnet assembly 12, enables the magnet elements 16 of the first zone 38 and the second zone 40 of the magnet assembly 12 to attract each other and eventually magnetically couple once the magnet assembly 12 is in the resection configuration.

As mentioned above, the magnet elements 16 can have various shapes and sizes. The choice of the shape and/or the size of the magnet elements 16 can depend on the target solid organ, and which portion of the organ, around which the resection device 10 will be implanted. For instance, for an organ like the liver that is substantially larger than an adrenal gland or a pancreas, and additionally has a right lobe that is substantially larger than the left lobe, elongated magnet elements 16 can be used as part of the magnet assembly 12. On the other hand, the length of the magnet element 16 can remain sufficiently small to permit the navigation of the magnet assembly 12 around the outer surface of the liver, or another target solid organ. For instance, in some implementations, magnet elements 16 designed to resection a portion of an adrenal gland can have a size ranging from about 2 mm to about 10 mm, whereas magnet elements 16 designed to resection a portion of a liver may have a size ranging from about 2 cm to about 13 cm. As a general relationship between the size of the magnet elements 16 and the target solid organ, magnet elements 16 designed to resection a solid organ that is thicker and/or larger can generally be larger than magnet elements 16 designed for a smaller and/or thinner solid organ. This general relationship takes into consideration the principle that larger and/or thicker solid organs may benefit from a larger attractive force conferred by larger magnet elements 16 to achieve a desired compression of the outer surface of the solid organ and subsequent separating of a portion of the solid organ at the edges surrounding the magnet elements 16. In some implementations, for a magnet assembly 12 configured in looped pre-resection configuration, magnet elements 16 may be longer than for a magnet assembly 12 configured in an extended pre-resection configuration, since in the looped pre-resection configuration, the magnet assembly 12 is already folded on itself. In some implementations, the magnet assembly 12 can vary in length to accommodate the size of the organ being resectioned. For example, a magnetic assembly 12 designed to resection a portion of an adrenal gland can be between about 3 cm and about 15 cm long, whereas a magnetic assembly 12 designed to resection a portion of a liver or a spleen can be between about 5 cm and about 30 cm long. A magnet assembly 12 designed to resection a portion of a kidney can be between about 10 cm to about 20 cm long, whereas a magnet assembly 12 designed to resection a portion of a pancreas can be between about 5 cm to about 20 cm long. When the zones 38, 40 of the magnet assembly 12 are in a continuous formation forming an enclosed shape, the size of the magnet assembly 12 can vary to accommodate the size of the desired resectioned portion.

In addition, although the magnet elements 16 of a portion of a magnet assembly 12 exemplified in FIGS. 3 and 11-16 are represented as being substantially rectangular, it is to be understood that the magnet elements 16 can include tapered edges, beveled edges, rounded edges, and the like. The magnet elements 16 can also have an oblong shape, stadium shape, a circular shape, a triangular shape, a rectangular shape, a trapezoidal shape, an octagonal shape or any other shape suitable for applications described herein.

Figure 17:
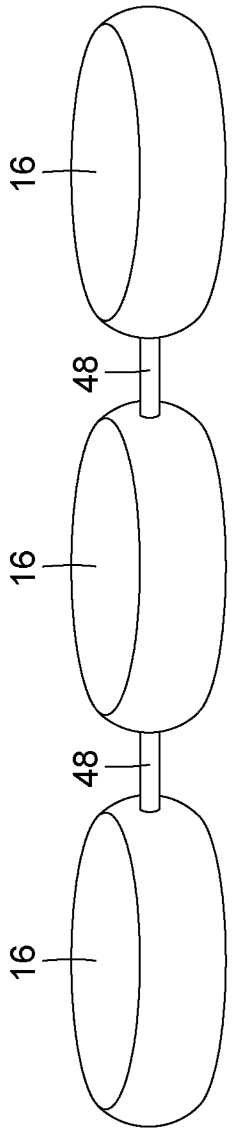
FIG. 17 is a perspective view schematic of three magnet elements of a portion of a magnet assembly shown in an arbitrary spatial relationship, each magnet element having rounded edges, and adjacent magnet elements being flexibly joined together by a flexible connector.

For instance, FIG. 17 illustrates an example of a series of magnet elements 16 of a portion of a magnet assembly 12, each magnet element 16 having rounded edges and a substantially oval shape. In some implementations, magnet elements 16 having rounded edges or other non-sharp features can contribute to facilitate movement between adjacent magnet elements 16 and thus provide an enhanced flexibility to the magnet assembly 12.

Figure 18:
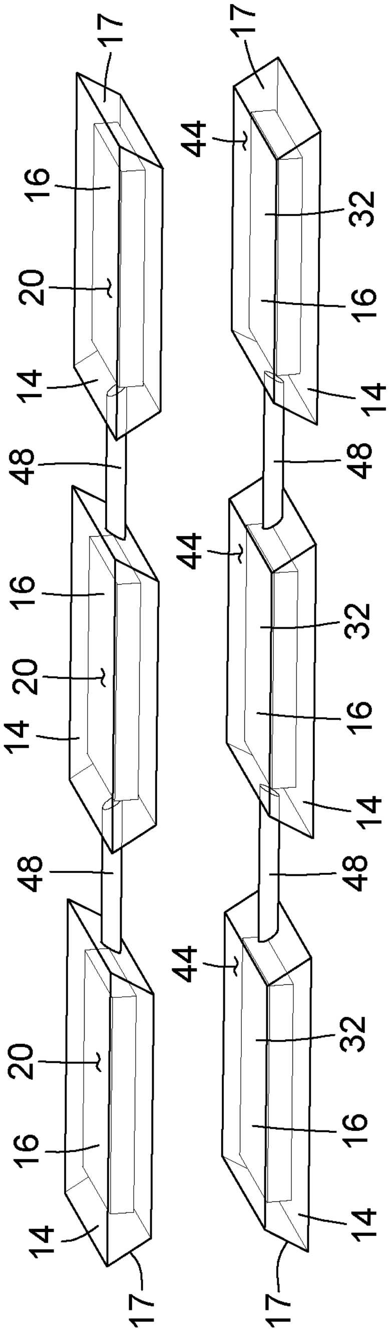
FIG. 18 is a perspective view schematic of six magnet elements of a portion of a magnet assembly shown in an arbitrary spatial relationship, each magnet element being received in a corresponding housing, the housing having bevelled edges, adjacent magnet elements being flexibly joined together by a flexible connector extending between corresponding housings, and the magnet elements being shown facing each other.

FIG. 18 illustrates an example of a series of magnet elements 16 of a portion of a magnet assembly 12, each magnet element 16 being received in a housing having beveled edges 17, the magnet elements 16 being shown facing each other as would be the case when placed on either side of the outer surface of the target solid organ.

Figure 19:
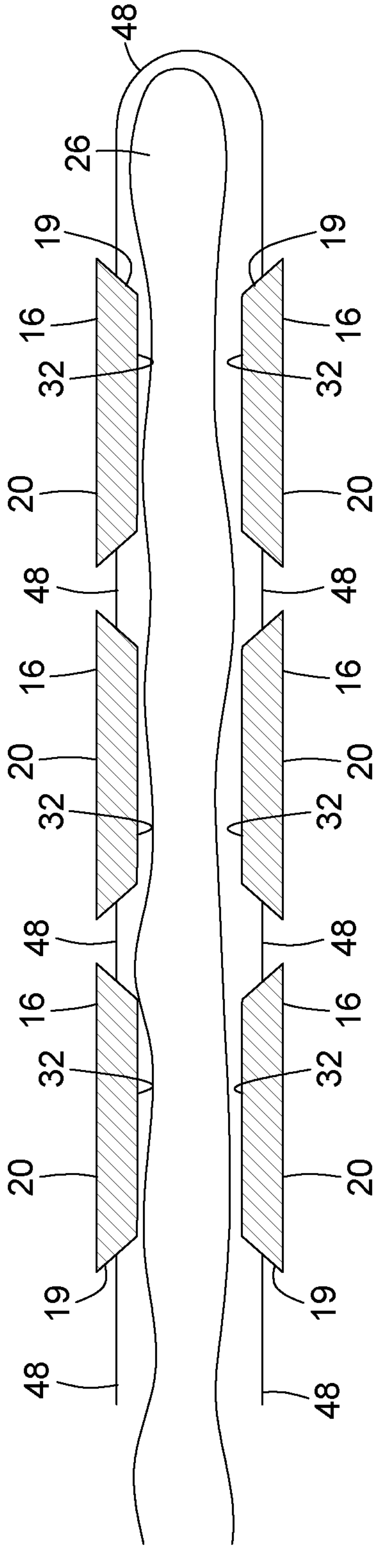
FIG. 19 is a side cross-sectional view schematic of six magnet elements of a portion of a magnet assembly shown in an arbitrary spatial relationship, each magnet element having bevelled edges, adjacent magnet elements being flexibly joined together by a flexible connector, the magnets being shown with opposing outer surfaces of a solid organ therebetween.

FIG. 19 illustrates an example of magnet elements 16 of a portion of a magnet assembly 12, each magnet element 16 having beveled edges 19 on the latitudinal side of the housing 14. In some implementations and as illustrated in FIG. 18 or 19, when magnet elements 16 or a housing 14 include beveled edges, the magnet-coupling side 32 of the magnet element 16 or the organ-contacting side 44 of the housing 14 can have a smaller surface area compared to the side located further away from the outer surface of the solid organ, i.e., the bottom side 20. This configuration can allow for a smaller compression surface between magnet-coupling sides 32 of opposite magnet elements 16 or between organ-contacting sides 44 of opposite housings 14, such that if the ischemic necrosis was to occur more rapidly than initially foreseen, the side of the magnet elements 16 or housings 14 having a larger surface area can provide an anchor to prevent undesired movements of the magnet elements 16 or housing 14. In some implementations, the side of the magnet elements 16 or housing 14 having a larger surface area can also contribute to prevent the magnet elements 16 or housing 14 to pass through an area of the walls of the solid organ where ischemic necrosis has occurred.

Figure 22:
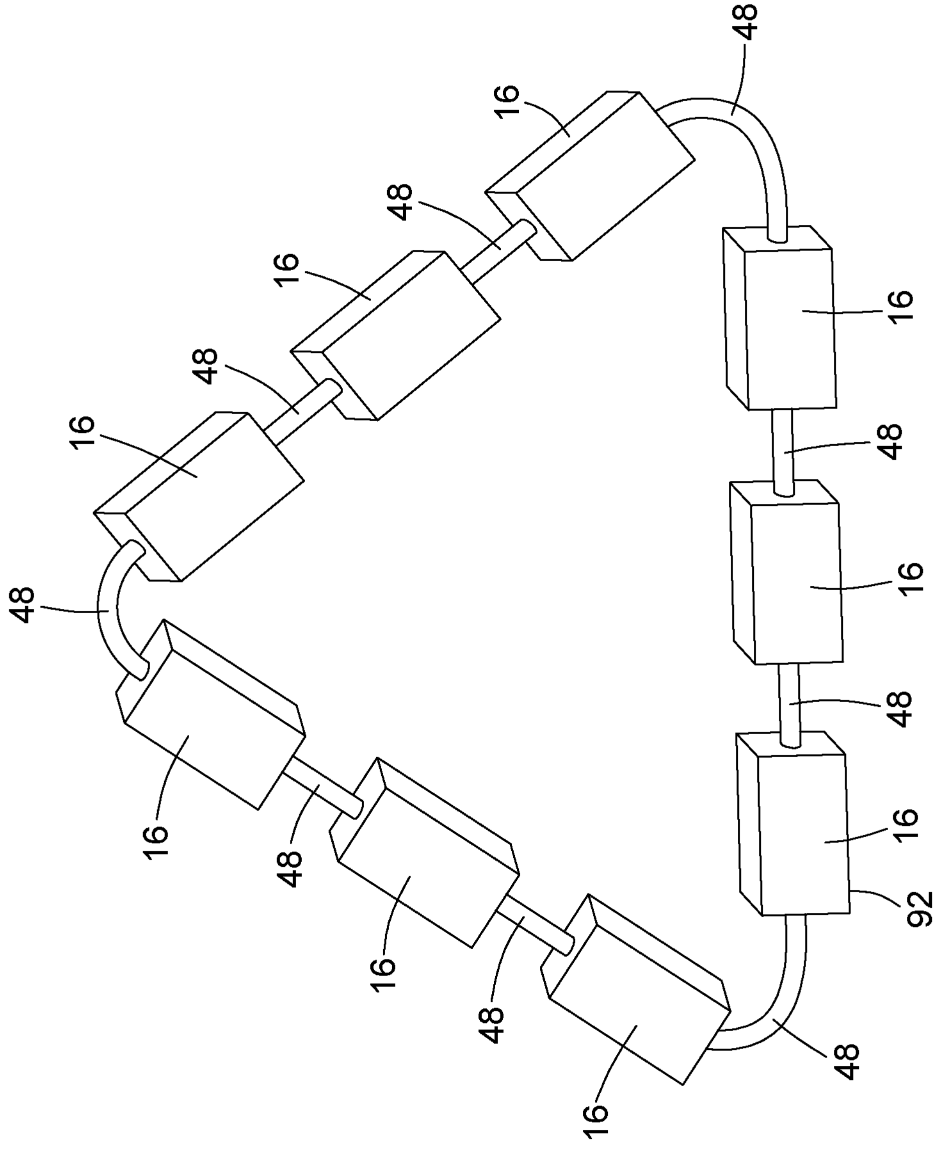
FIG. 22 is a perspective view schematic of magnet elements of a portion of a magnet assembly shown in a continuous formation forming an enclosed triangular shape, and the magnet elements being flexibly joined together by a flexible connector extending between adjacent magnet elements.

In some implementations, the magnet elements 16 connected in series can be arranged linearly, such as shown in FIGS. 1 to 10. When referring to magnet elements 16 that are arranged linearly, it is meant that the magnet elements 16 can alternate between an extended pre-resection configuration or looped pre-resection configuration and a resection configuration. In other implementations, the magnet elements 16 can be linked or joined together such that the magnet elements 16 are arranged in a substantially continuous formation forming an enclosed shape. The enclosed shape of the magnet elements can be determined according to a shape corresponding to the shape of a desired resectioned portion. In the implementation shown in FIG. 22, the enclosed shape of the magnet elements 16 is a substantially triangular shape. It is to be understood that the magnet elements can be arranged in a continuous formation forming any type of enclosed shape, such as circular, square, rectangular, rhomboidal, pentagonal, etc. In some implementations, the enclosed shape of the magnet elements 16 can be an irregular shape that generally corresponds to the shape of the desired resectioned portion, which in turn can be determined in accordance with the shape of a lesion or tumor that is being resectioned from the organ. The magnet elements 16 forming the enclosed shape can be connected via a flexible connector 48, such as string. The type of flexible connector 48 can be chosen to provide sufficient mobility and flexibility to the magnet assembly 12 according to a given range of movement, so that the magnet assembly 12 can easily be guided to its destination in the body cavity and placed around the target solid organ.

When referring to a first zone 38 of magnet elements 16 and a second zone 40 of magnet elements 16 when the magnet elements 16 are provided in an enclosed shape, the first zone 38 corresponds to a first set of magnet elements 16 that is configured for placement against a first side of the target solid organ, and the second zone 40 corresponds to a second set of magnet elements 16 that is configured for placement against a second side of the target solid organ, the first and second sets of magnet elements 16 together forming a magnet assembly 12.

In some implementations, magnet elements 16 provided in an enclosed shape for each zones 38, 40 can be connected via a solid or semi-solid connector to retain the enclosed shape of the continuous formation. The solid or semi-solid connector can be chosen to provide sufficient stability to the magnet assembly 12 and prevent or lessen a range of movement, such that the magnet assembly 12 can retain the enclosed shape of the continuous formation when placed against the target solid organ. Alternatively, the solid or semi-solid connector can be chosen to have some flexibility to facilitate a range of movement when placing the resection device 10 against the outside of the organ, while still retaining the outline of the enclosed shape.

The magnet elements 16 in the first zone 38 can be connected via a flexible connector 48 to the magnet elements 16 in the second zone 40 such that when the resection device 10 is inserted in the body cavity, the first zone 38 is positioned along an enclosed resection line on a first portion of the organ, such as an interior or peripheral region on the anterior portion of the organ, and the second zone 40 is positioned along a corresponding enclosed resection line on a second portion of the organ, such as an interior or peripheral region on the posterior portion of the organ, with the flexible member 48 extending between the two zones 38, 40 around the periphery of the organ. Alternatively, the first zone 38 and the second zone 40 can be separate continuous magnet element 16 formations that are placed on either side of the solid organ at corresponding enclosed resection lines and are only coupled within the body cavity through the magnetic coupling of the magnet-coupling sides 32 of the magnet elements 16 in the first zone 38 and the second zone 40.

In another implementation, when the magnet elements 16 form an enclosed shape that can be folded against an outer periphery of the solid organ, the magnet elements 16 of the first zone 38 that are configured to be positioned along the periphery of the organ can be coupled, for example, with a flexible connector 48, to the magnet elements 16 of the second zone 40. Thus, when the resection device 10 is used to resection a portion of the solid organ along the periphery of the organ, the first zone 38 and the second zone 40 can fold around the periphery of the organ along the resection line outlining a resectioned portion on the periphery of the organ with the magnet elements 16 of the first zone 38 being flexibly connected to the magnet elements of the second 40 to enable the folding of the magnet assembly. In yet another implementation, the magnet assembly 12 can comprise magnet elements 16 provided as an enclosed shape that is configured to fold around a periphery region of the target solid organ, such that the magnet elements 16 provided in a first zone 38 are positioned on, i.e., against, one side of the organ's periphery, such as an anterior side, and the magnet elements 16 of a second zone 40 are positioned on, i.e., against, an opposite side of the organ's periphery, such as the posterior side, so as to compress the organ in between. For example, when a resection line viewed individually from an anterior side and a posterior side forms a triangle with the periphery of the organ, the magnet assembly 12 can have a rhombus shape, such that the magnet elements 16 in the first zone 38 form a first triangle within the rhombus shape and the magnet elements 16 of the second zone 40 form a second triangle within the rhombus shape. Thus, when the magnet elements 16 of the first zone 38 and the second zone 40 are folded around the periphery of the organ, the magnet elements 16 in the first zone 38 can magnetically couple to the magnet elements 16 in the second zone 40.

In some implementations, the magnet-engaging side 32 of the magnet elements 16 included in the first zone 38 of the magnet assembly 12 can have a complimentary shape with regard to the magnet-engaging side 32 of the magnet elements 16 included in the second zone 40 of the magnet assembly 12. For instance, the magnet-engaging side 32 of the magnet elements 16 included in the first zone 38 can include a recess, and the magnet-engaging side 32 of the magnet elements 16 included in the second zone 40 can include a projection configured to fit within the recess. In some implementations, the engagement of the recess with a corresponding projection, or of other features having complimentary shape, can contribute to stabilizing the magnet elements 16 of the first zone 38 with those of the second zone 40. In other implementations, the engagement of the recess with a corresponding projection, or of other features having a complimentary shape, can facilitate the resection of the solid organ such that separation of the resectioned portion from the retained portion of the solid organ can be facilitated. In other implementations, the resectioned portion can be partially attached to the retained portion of the organ, such as with loose or areolar connective tissue or scar tissue, when the resection device 10 is removed, in which case the resectioned portion can be removed from the remaining portion of the organ by other means, such as with a cutting means, e.g., a scalpel. In some implementations, the edges of the magnet elements 16 included in the first zone 38 of the magnet assembly 12 can include a rabbeted edge, and the edges of the magnet elements 16 included in the second zone 40 of the magnet assembly 12 can include a rabbeted edge that is complimentary to the one of the magnet elements 16 of the first zone 38.

In some implementations and as mentioned above, the attractive force of the magnet elements 16 can be chosen according to the thickness and/or to the composition of the target solid organ along the resection line 42. For instance, the attractive force of the magnet elements 16 can be proportional to the thickness or shape of the target solid organ. This principle can apply from one target solid organ to another, or within the same target solid organ. For example, as the right lobe of the liver is thicker than the left lobe, the attractive force of the magnet elements 16 for a magnet assembly 12 designed to remove the right lobe of the liver may be higher than for a magnet assembly 12 designed to remove the left lobe of the liver or a smaller organ, such as the pancreas.

In some implementations, the attractive force of the magnet elements 16 can vary within the first zone 38 and accordingly within the second zone 40 such that the pressure exerted on the target solid organ along the length of the magnet assembly 12 once in the resection configuration can also vary. For instance, when the target solid organ is the kidney, the regions of the kidney that are closer to the outer periphery of the kidney can be thicker than a central region of the kidney. Accordingly, the magnet elements 16 of the magnet assembly 12 can be chosen to have a higher attractive force in a first segment of the magnet assembly 12 that is closer to the transition from the first zone 38 to the second zone 40 compared to the attractive force of the magnet elements 16 of the magnet assembly 12 in a second segment of the magnet assembly 12 that is away from the transition from the first 38 to the second zone 40. This can apply for instance to solid organs that have generally thicker outer periphery portions compared to the thickness near a central portion of the solid organ. In other implementations, the magnet elements 16 of the magnet assembly 12 can be chosen to have a higher attractive force in a middle segment of the magnet assembly 12 compared to the attractive force of the magnet elements 16 of the magnet assembly 12 on either side of the middle segment. This can apply for instance to solid organs that have a generally thicker central portion compared to the thickness of outer periphery portions of the solid organ. When the desired resectioned portion of the target solid organ is along its periphery, the magnet elements 16 located away from the outer periphery of the solid organ can be chosen to have a higher attractive force compared to the attractive force of the magnet elements 16 closer to the outer periphery of the solid organ, or vice versa.

The attractive force of the magnet elements 16 can also be chosen so as to facilitate placement and implantation of the resection device 10 around the target solid organ. For instance, in some implementations, the attractive force between at least a portion of the magnet elements 16 can be sufficiently weak to enable magnetic uncoupling of the magnet elements 16 during the placement of the resection device 10 along the resection line 42, such that trial and error may be possible to arrive at the desired location of the magnet assembly 12.

Furthermore, the attractive force of the magnet elements 16 can also be chosen in function of the duration of the planned healing period. It is to be understood that the healing period can be considered to be initiated when magnet elements magnetically couple to each other starting from the outer periphery of the solid organ, and continues as magnet elements magnetically couple to each other progressively closer to the central region of the solid organ over time until all magnet elements are magnetically coupled to each other along the resection line. For example, the attractive force between the magnet elements 16 can be sufficiently weak to favor a healing period in a range of days or weeks. In some implementations, the healing period can be determined such that the retained portion side of the organ can progressively succumb to the ischemic pressure and become necrotic, and the remaining portion of the organ can progressively heal. A longer healing period can reduce the bleeding as a progressive application of pressure along the resection line can enable a portion of the target solid organ that first succumbs to ischemic pressure necrosis, such as the outer regions of the organ, to heal while the internal portion of the target solid organ is still being subjected to ischemic pressure forces. Magnet elements 16 that have too strong of an attractive force could cause rapid ischemic pressure necrosis along the resection line 42 (i.e., between the magnet-coupling sides 32 of the magnet elements 16), which could cause increased bleeding and/or impair the healing mechanism along the resection line (i.e., on the edges of the magnet elements 16). In some implementations, the attractive force of the magnet elements 16 can be chosen such that the compression process occurs over a period of between about 1 to about 6 weeks following implantation of the resection device 10. In some implementations, the attractive force of the magnet elements 16 is chosen such that the compression process occurs over a period of between 10 to 20 days following implantation of the resection device 10. Other durations of compression periods are also possible depending on the desired result and the target solid organ.

It is to be noted that in some implementations, the ischemic pressure necrosis to which the target solid organ is subjected to along the resection line 42 may be sufficient to lead to a progressive transection of the target solid organ and thus separation of the resectioned portion from the retained portion of the target solid organ. In other implementations, the progressive pressure to which the outer surface of the target solid organ is subjected to along the resection line 42 may be sufficient to lead to a partial separation of the resectioned portion of the retained portion of the target solid organ. The attractive force of the magnet elements 16 can thus also be chosen according to whether a complete or partial separation of the resectioned portion of the target solid organ is desired.

Monitoring the healing process through time also plays a role in the result obtained on the target solid organ following the implantation of the resection device 10, and such monitoring can be helpful in determining at which moment to proceed with the removal of the resection device 10 to obtain the desired result with regard to the resection of the target solid organ (i.e., the separation of the resectioned portion from the retained portion of the target solid organ).

In some implementations, the size and/or shape of the magnet elements 16 can vary along the length of the magnet assembly 12. This variation in the size and/or shape of the magnet can contribute to increase the flexibility of the magnet assembly 12 in selected portions thereof, in particular when the magnet assembly 12 includes multiple magnet elements 16 individually received in a housing 14 or without a housing, such as shown in FIGS. 12-15 and 18. For instance, the magnet assembly 12 can include smaller magnet elements 16 in proximity of the transition from the first zone 38 to the second zone 40. Smaller magnet elements 16 provided in proximity of this transition zone can contribute to facilitate the adoption of the looped pre-resection configuration and the resection configuration, by facilitating the folding over of the magnet assembly 12 such as shown in FIG. 7. Smaller magnet elements 16 in proximity of the transition from the first zone 38 to the second zone 40 can thus facilitate the placement of the resection device 10. In some implementations, larger magnet implants, especially in terms of length, away from this transition zone can facilitate the obtention of a continuous resection line 42.

Housing

Figure 11:
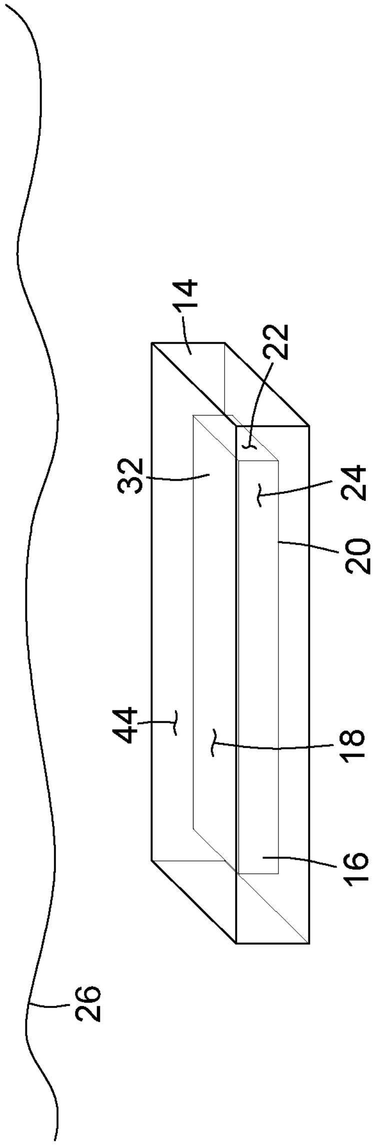
FIG. 11 is a perspective view schematic of a magnet element shown in an arbitrary spatial relationship relative to an outer surface of a portion of a solid organ, the magnet element being received in a corresponding housing.

With reference to FIGS. 11-16 and 18, in some implementations, the magnet elements 16 can be received in a housing 14. In FIG. 11, a single magnet element 16 is received in a corresponding housing 14, while in FIG. 12, multiple magnet elements 16 are received in a single housing 14. In other implementations, a certain number of magnet elements 16 can be received in a housing 16. For instance, 2 to 10 magnet elements 16 can be received in a single housing 14. In such implementations, the number of magnet elements 16 in the housing 14 can be influenced by their size, i.e., the smaller the magnet elements 16, the more successive magnet elements 16 can be received in a housing 14 having a given length.

Figure 13:
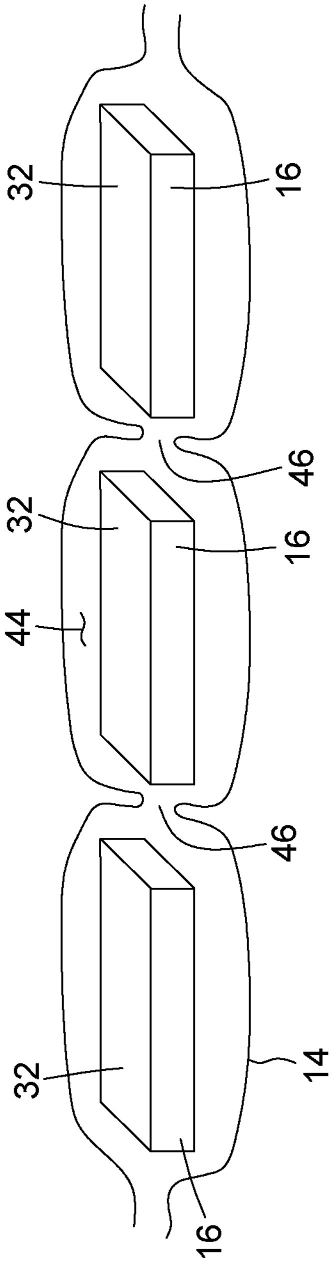
FIG. 13 is a perspective view schematic of three magnet elements of a portion of a magnet assembly shown in an arbitrary spatial relationship, the magnet elements being received in a corresponding housing having rounded edges, the successive housings being flexibly joined together by a thinner extension of the housing.

As mentioned above, the housing 14 includes an organ-contacting side 44 that is in contact with the tissue of the target solid organ when the resection device 10 is in the resection configuration. In some implementations, the organ-contacting side 44 of the housing 14 includes an elongated flat contact surface to facilitate an even contact with the tissue compressed therebetween. The housing 14 can be configured to provide an atraumatic surface which can contribute to avoid damage to surrounding tissues. The housing 14 can include rounded edges, and/or tapered transitions between its walls. In some implementations, the housing 14 can have an oblong shape or a stadium shape. FIG. 13 illustrates an example of magnet elements 16 received in a respective housing 14 having rounded edges, the successive housings 14 being flexibly joined together by a thinner extension 46 of the housing 14, also referred to as a connecting portion of the housing 14. Additional details are provided below regarding this aspect.

Figure 23B:
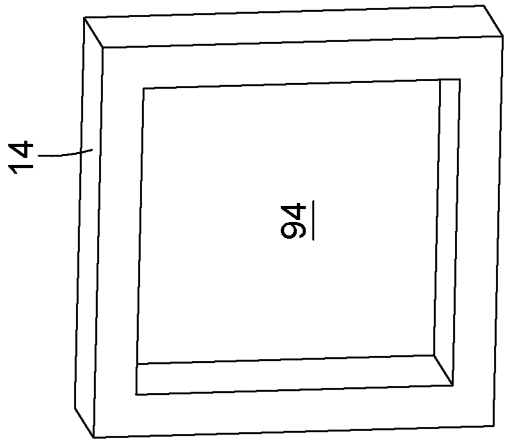
FIG. 23B is a perspective view schematic of a housing having an enclosed quadrilateral shape.
Figure 23A:
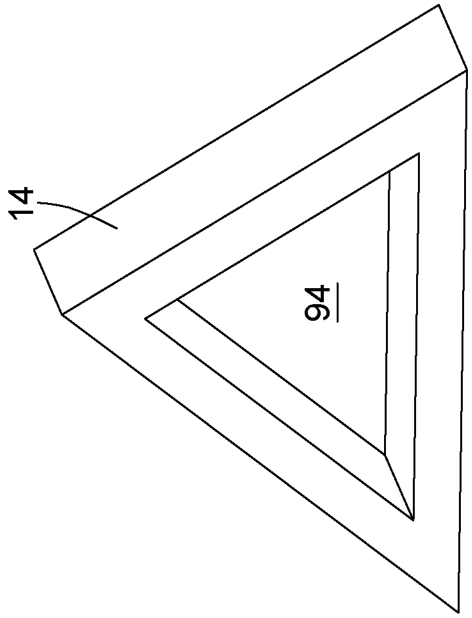
FIG. 23A is a perspective view schematic of a housing having an enclosed triangular shape.

In some implementations, such as shown in FIGS. 23A and 23B, the housing 14 can be configured to form an enclosed shape that corresponds to the shape of the desired portion that is desired to be resectioned from the solid organ (i.e., corresponding to the desired size and shape of the resectioned portion). The enclosed shape can define a through hole or an opening 94 for instance to allow space for the lesion 90 as the magnet elements 16 of the first zone 38 and the magnet elements 16 of the second zone 40 slowly magnetically couple. Alternatively, the enclosed shape can have a continuous contact surface, i.e., a solid contact surface without an opening defined therethrough.

In FIG. 23A, the housing 14 is configured to hold the magnet elements 16 in a substantially triangular shape. In FIG. 23B, the housing is configured to hold the magnet elements 16 in a substantially quadrilateral shape, for example in a square shape. In this implementation, the magnet elements 16 in the first zone 38 can be contained within a single housing 14 and the magnet elements 16 in the second zone 40 can be contained within a separate housing 14. The zones 38, 40 can be separate from each other or can be connected with a flexible connector 48. Alternatively, the housing 14 can be configured to contain magnet elements 16 from both the first zone 38 and the second zone 40 with a flexible transition zone, such that the first zone 38 and the second zone 40 can be magnetically coupled to each other. For example, the housing 14 can include portions in between adjacent magnet elements 16 along a first side 92 of the first zone 38 and the second zone 40 that are adapted to provide an increased flexibility to the magnet assembly 12. These portions can be narrower, or thinner, to increase their freedom of movement, while remaining sufficiently robust to avoid breaking. The portion of the housing 14 between adjacent magnet elements 16 or between adjacent first sides 92 can, for example, enable the magnet assembly 12 to fold around the target solid organ.

In some implementations, the organ-contacting side 44 of the housing 14 of the magnet elements 16 included in the first zone 38 can include a recess, and the organ-contacting side 44 of the housing 14 of the magnet elements 16 included in the second zone 40 can include a projection configured to fit within the recess. The engagement of the recess with a corresponding projection, or of other features having complimentary shape, via the housings 14 can contribute to stabilize the magnet elements 16 of the first zone 38 with those of the second zone 40, thus facilitating the stability of the resection device 10 during the compression of the organ at the resection line 42. In some implementations, the edges of the organ-contacting side 44 of the housing 14 of the magnet elements 16 included in the first zone 38 of the magnet assembly 12 can include a rabbeted edge, and the edges of the organ-contacting side 44 of the housing 14 of the magnet elements 16 included in the second zone 40 of the magnet assembly 12 can include a rabbeted edge that is complimentary to the one of the housings 14 of the first zone 38.

In some implementations, the housing 14 can contribute to spreading the force applied by the magnet element(s) 16 over a larger area, which can be advantageous depending on the application and/or on the target solid organ. The housing 14 can be made of a biocompatible material. In some implementations, the housing 14 can be made of a metal such as stainless steel, titanium, or other medical implant grade metals. Alternatively, the housing 14 may be made of silicone, or other medical implant grade polymers. In certain scenarios, the housing 14 is made of Silastic™, which is a flexible silicone elastomer. In some implementations, the housing 14 can provide a protective coating around the magnet element(s) 16, which in turn can help preventing corrosion and maintaining the integrity of the magnet element 16. The texture of the housing 14, in particular on the organ-contacting side 44, can be chosen to provide an increased stability to the magnet assembly 12 once in the resection configuration. For instance, the surface roughness of the implant on the organ-contacting side 44 of the housing 14 can be higher than on the opposite side thereof. The surface roughness of the organ-contacting side 44 of the housing 14 may be beneficial once the magnet elements 16 are magnetically coupled to prevent magnetic decoupling due to shear forces.

Flexible Connection Between Adjacent Magnet Elements

As mentioned above, the magnet assembly 12 includes magnet elements 16 that are flexibly connected to each other in series. Flexibly connecting the magnet elements 16 together can be achieved in various ways. Examples are provided below.

With reference to FIG. 13, multiple magnet elements 16 can be received in a respective single housing 14, and the housing 14 can include portions in between adjacent magnet elements 16 that are adapted to provide an increased flexibility to the magnet assembly 12. As shown in FIG. 13, these portions 46 can be narrower, or thinner, to increase their freedom of movement, while remaining sufficiently robust to avoid breaking. In some implementations, the portion 46 of the housing 14 between adjacent magnet elements 16 can be made of a material that is different from the material of the rest of the housing 14, to benefit from specific characteristics of this different material, in particular in terms of its flexibly. In some implementations, the portion 46 of the housing 14 between adjacent magnet elements 16 can offer a certain range of motion in a certain plane, while offering a restricted range of motion in another plane. For example, it may be desired to have the magnet elements 16 move relative to each other to enable the magnet assembly 12 to fold around the target solid organ, while it may be less desirable to have the magnet elements 16 move laterally relative to each other, as lateral movement of the magnet elements 16 could contribute to veering the magnet elements 16 off of the resection line 42.

Figure 14:
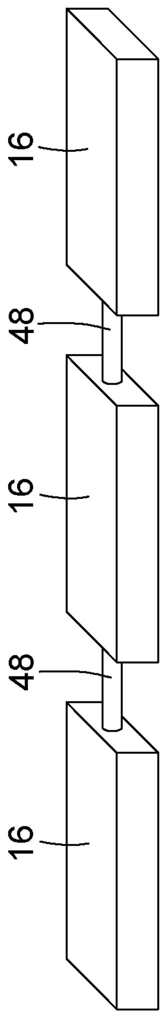
FIG. 14 is a perspective view schematic of three magnet elements of a portion of a magnet assembly shown in an arbitrary spatial relationship, adjacent magnet elements being flexibly joined together by a flexible connector.

With reference to FIG. 14, when no housing is provided around the magnet elements 16, the magnet elements 16 can include a hook (not shown) on each lateral side thereof, and be connected to each other via a flexible connector 48, such as a string. The type of flexible connector 48 can be chosen to provide sufficient mobility and flexibility to the magnet assembly 12 according to a given range of movement, so that the magnet assembly 12 can easily be guided to its destination in the body cavity and placed around the target solid organ. For example, when the target solid organ is a gland such as the adrenal gland, the circumference of such organs can be relatively small compared to the size of other organs, such as the kidney or liver. Accordingly, it may be beneficial to have a magnet assembly 12 that has an increased flexibility to facilitate guiding the resection device 10 around the organ and maintaining it in place.

Figure 15:
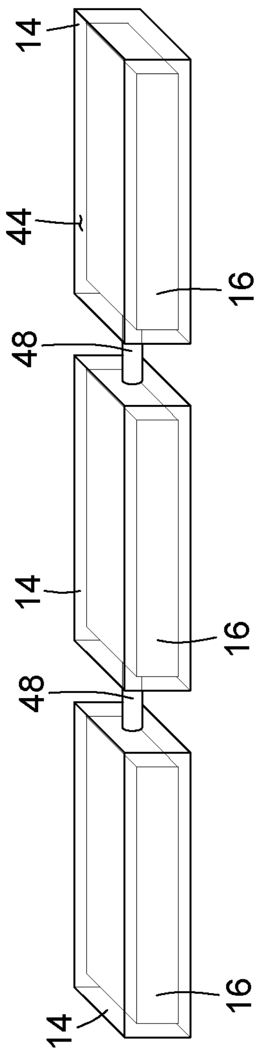
FIG. 15 is a perspective view schematic of three magnet elements of a portion of a magnet assembly shown in an arbitrary spatial relationship, each magnet element being received in a corresponding housing, and adjacent magnet elements being flexibly joined together by a flexible connector extending between corresponding housings.

With reference to FIG. 15, a flexible connector 48 can be provided between adjacent magnet elements 16 that are individually housed in a respective housing 14. In such implementations, an engaging portion, such as a hook (not shown), can be provided on the lateral sides of the housing 14. In some implementations, the engaging portion can be integral with the housing 14. The housing 14 can thus be molded as a single piece unit that includes a hook on each lateral side thereof, with the magnet element 16 received in the housing 14, and adjacent ones of the multiple magnet elements 16 can be flexibly connected to each other via a flexible connector 48 engaged with respective hooks. Alternatively, a hook can be provided on a lateral side of the housing 14, and a flexible connector 48 can extend from another side to flexibly connect with a hook of an adjacent housing 14. In some implementations, the engaging portion can be provided on one or more lateral sides of the housing to couple the magnet elements 16 in a continuous formation forming an enclosed shape.

In implementations where the magnet elements 16 form an enclosed shape and the magnet assembly includes a first set of magnet elements 16 provided in a first zone 38 and a second set of magnet elements 16, distinct from the first one, provided in a second zone 40, the magnet elements 16 can be connected with a flexible connector 48 to facilitate positioning the magnet elements 16 precisely against the portion of the organ being resectioned. In this implementation, when the magnet elements 16 in the first zone 38 are uncoupled from the magnet elements 16 in the second zone 40, such as prior to being positioned against the solid organ, the magnet elements 16 may form a loose or slacked shape. Thus, when the resection device 10 is positioned on the resection line on the target solid organ the resection line also forming an enclosed shape, the magnet elements 16 of the first zone 38 and the magnet elements 16 from the second zone 48 can be positioned on opposing sides of the target organ in a shape that corresponds to the shape of the desired resectioned portion, i.e., of the desired resection line, which can be for example a triangular resection line or a quadrilateral resection line.

In other implementations where the magnet elements 16 are arranged in a continuous formation, the magnet elements can be connected with a solid, semi-solid, or semi-flexible connector configured to retain the enclosed shape.

Figure 16:
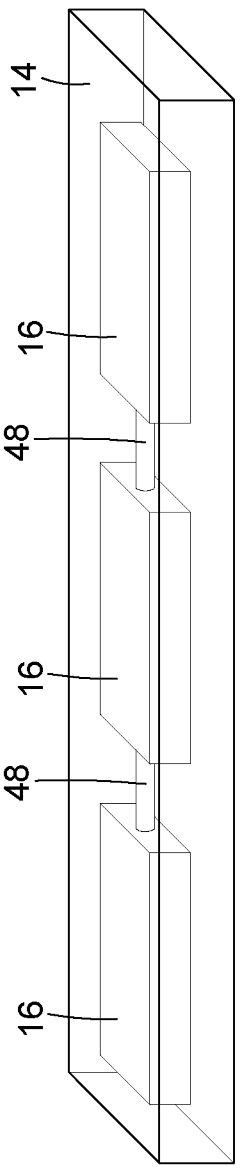
FIG. 16 is a perspective view schematic of three magnet elements of a portion of a magnet assembly shown in an arbitrary spatial relationship, the magnet elements being received in a corresponding housing, and the magnet elements being flexibly joined together within the housing by a flexible connector extending between adjacent magnet elements.

In other implementations and with reference to FIG. 16, the magnet elements 16 can be flexibly connected to each other by being integrated within the housing 14, and a flexible connector 48 can also be provided between adjacent magnet elements 16 within the housing 14. In the implementation shown in FIG. 16, in contrast to the implementation shown in FIG. 15, the flexible connectors 48 are thus shown integrated within the housing 14.

Figure 12:
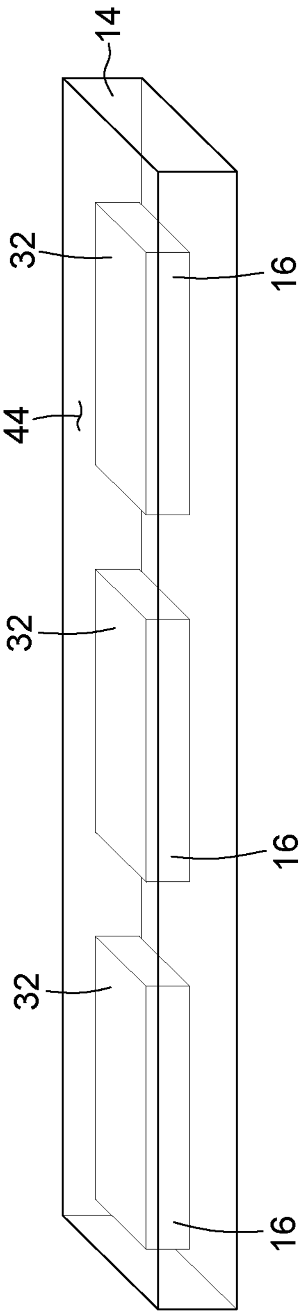
FIG. 12 is a perspective view schematic of three magnet elements of a portion of a magnet assembly shown in an arbitrary spatial relationship, the magnet elements being received in a single housing.

It is to be understood and as shown in FIG. 12, that the flexibility of the magnet assembly 12 can be provided by the presence of the housing 14 itself around the magnets elements 16, for instance given the flexibility of the material from which is made the housing 14.

The distance between adjacent magnet elements 16 can be chosen so as to have an impact on the resulting flexibility of the magnet assembly 12. In some implementations, when determining the distance between adjacent magnet elements 16, care should be taken to maintain an equilibrium between the flexibility of the magnet assembly 12 obtained in such manner and the impact on the resulting resection line 42, as successive magnet elements 16 that may be too distant apart from each other may result in a less uniform resection line 42. In some implementations, the distance between adjacent magnet elements 16 can vary along the length of the magnet assembly 12, similarly to what is described above regarding the size of the magnet elements 16. For instance, in some implementations, magnet elements 16 located in proximity of the transition from the first zone 38 to the second zone 40 may be provided slightly further apart to provide enhanced flexibility to the magnet assembly 12 in this transitioning area. In some implementations, the interplay between the size of the magnet elements 16 and the distance between adjacent magnet elements 16 can contribute to provide an enhanced flexibility to the magnet assembly 12 and a desired resection line 42. In some implementations, magnet elements 16 provided as close as possible to each other can be favored as long as flexibility of the magnet assembly 12 is preserved. In that respect and as mentioned above, magnet elements 16 or housings 14 having rounded edges can be advantageous to provide magnet elements 16 or housings 14 close together but without compromising flexibility of the magnet assembly 12. It is to be noted that these are examples only to illustrate the effect that the various configurations may have on the flexibility of the magnet assembly 12, and that multiple configurations of the magnet assembly 12 can be implemented to achieve a combination of a desired flexibility of the magnet assembly 12 and a desired resection line 42 and corresponding healing of the tissue on the edges of the magnets elements 16.

Positioning and Implantation of the Resection Device

With reference now to FIGS. 20-29, implementations related to the implantation of the resection assembly at various locations for a given target solid organ, and for different target solid organs, will be now described.

Figure 20:
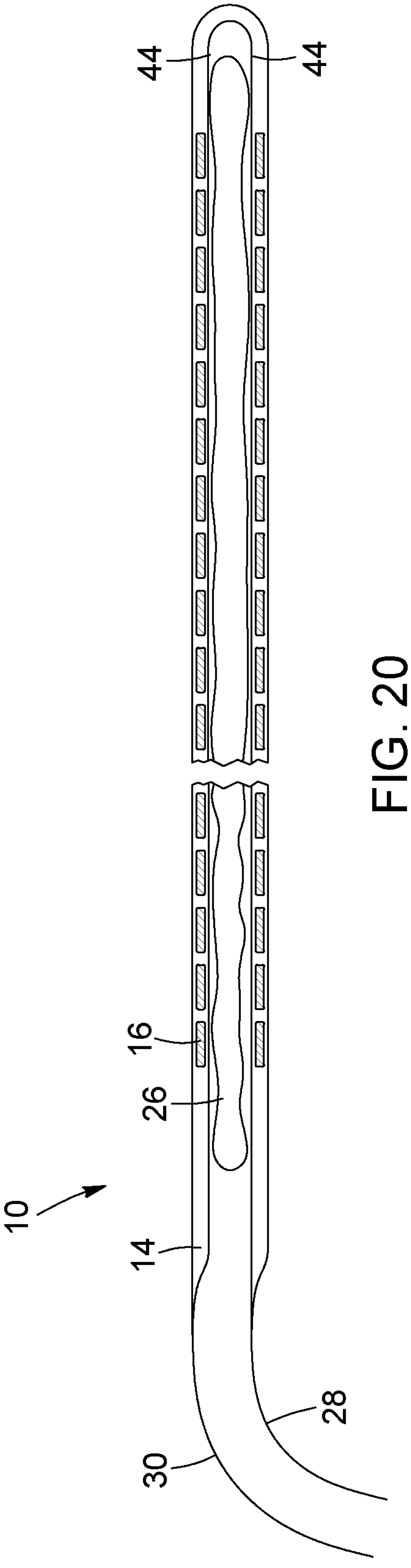
FIG. 20 is a side cross-sectional view schematic of a resection device that includes magnet elements received in a housing having an elongated flat contact surface on an organ-contacting side thereof, the resection device being shown in a resection configuration with the outer surfaces of a solid organ being compressed between the elongated flat contact surfaces.

FIG. 20 illustrates an example of a resection device 10 in a resection configuration, with opposite outer surfaces of the target solid organ being compressed between the organ-contacting sides 44 of the housing 14, and the magnet-engaging sides 32 of the magnet elements 16 from the first zone 38 being magnetically attracted to the magnet-engaging sides 32 of the magnet elements 16 from the second zone 40. The resection device 10 can be implanted along a desired resection line 42, and examples of locations of the resection line 42 are provided below.

Figure 21:
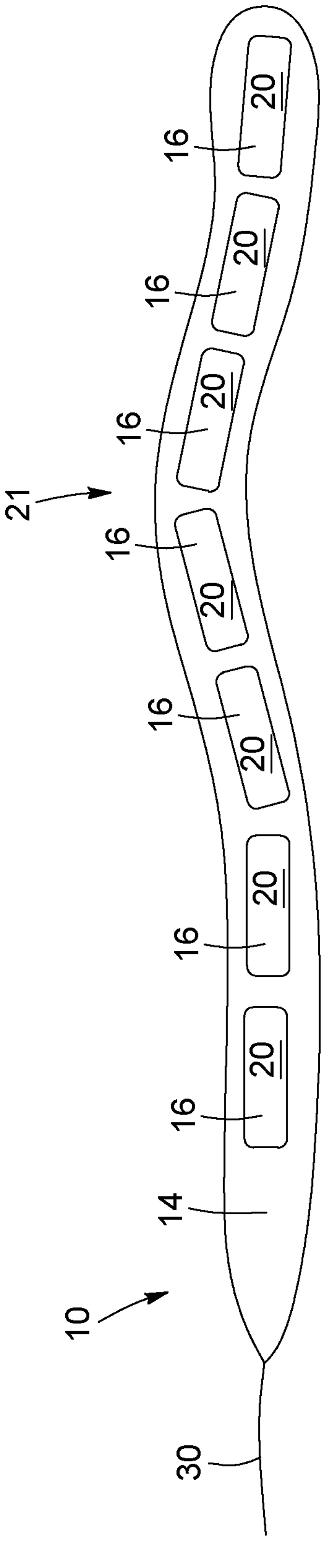
FIG. 21 is a top view schematic of a resection device that includes magnet elements, the magnet elements being arranged to provide a curved region along the length of the portioning device.

FIG. 21 illustrates an example of a resection device 10 in a resection configuration, showing a top view of the resection device 10. The resection device 10 shown in FIG. 21 includes a curved region 21. The curved region 21 can be provided for instance by the shape of the housing 14, or by the way the magnet elements 16 are joined together. In some implementations, curved magnet elements 16 can also be provided. The shape and location of the curved region 21 can vary, and FIG. 21 is only an example shown for illustrative purposes. This type of configuration of the resection device 10, i.e., a resection device 12 that includes a curved region 21, can be advantageous for placement of the resection device 12 around a tumor, for instance.

Figure 24B:
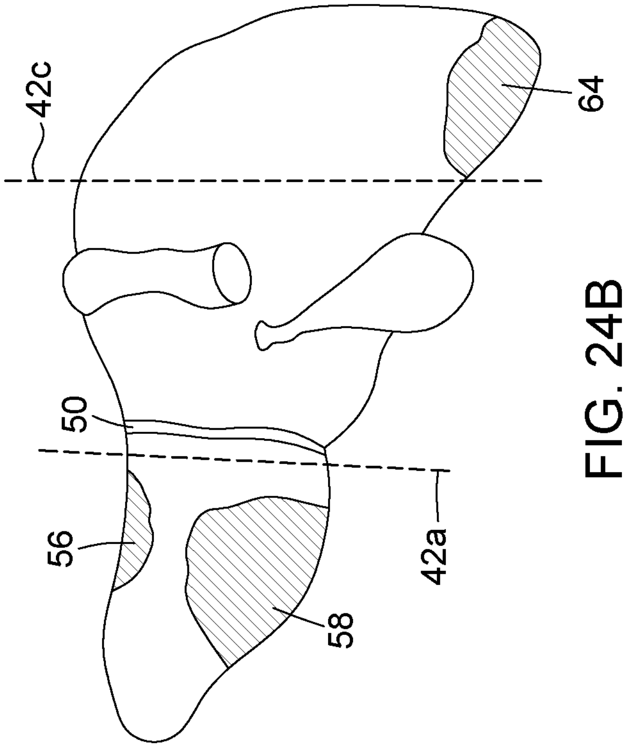
FIG. 24B is a posterior view schematic of a liver, showing transverse resection lines for right and left lobe hepatectomies.
Figure 24A:
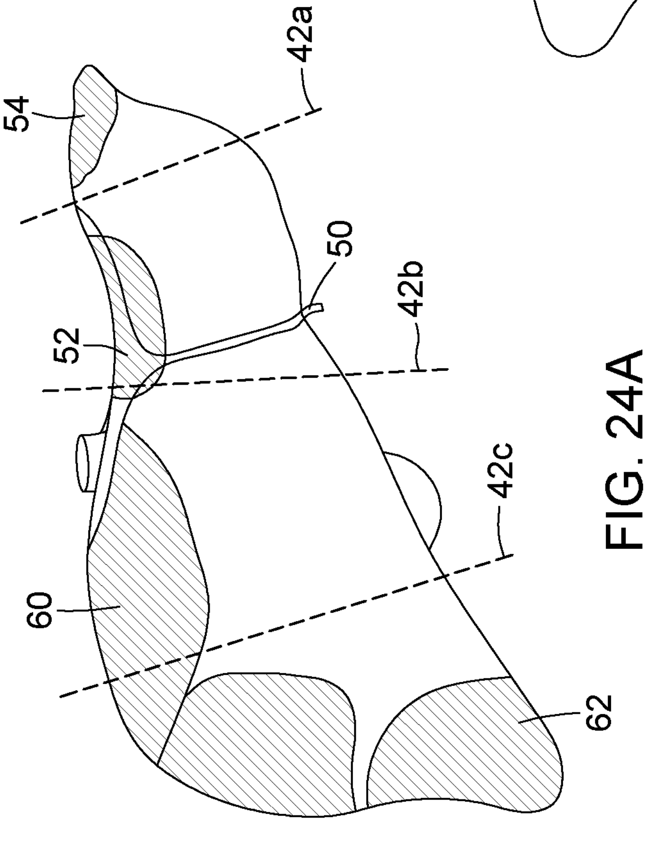
FIG. 24A is an anterior view schematic of a liver, showing transverse resection lines for right and left lobe hepatectomies.

FIGS. 24A and 24B show an anterior and posterior view, respectively, of a liver. An example of a vertical resection line 42*a* is shown. The magnetic device 10 can be implanted along vertical resection line 42*a* to facilitate the removal of a portion of the left lobe of the liver, such as during a left lobectomy or a left lateral segmentectomy where the portion of the liver medial to the umbilical fissure (i.e., sections II and III of the Couinard classification system) is removed. Resection line 42*a* can extend from a superior side of the left lobe (generally defined as the lobe of the liver that is distinct from the right lobe and separated therefrom by the falciform ligament 50; the left lobe being medial to the right lobe), for example, between a cardiac area 52 and a left dome 54 on the anterior side of the liver and lateral to a esophageal impression 56 on the posterior side of the liver, to the inferior side of the left lobe, for example lateral to a gastric impression 58 on the posterior side of the liver. Use of the resection device 10 along resection line 42*a* can, over time, result in the progressive separation of a portion of the left lobe of the liver following healing of the tissue on the edges of the magnet elements 16.

The location of the resection line 42 can vary depending on the size of the portion of the solid organ that is desired to be removed. For example, in FIGS. 24A and 24B with reference to a liver, when the entire left lobe is removed in a left hepatectomy (i.e., the sections medial to the Cantlie's line or sections II, III, IVa and IVb of the Couinaud classification system), the magnetic device 10 can be positioned along resection line 42*b*. Resection line 42*b* can extend from the superior side of the left lobe of the liver, for example lateral to the vena cava area 52, to the inferior side of the left lobe near the gallbladder, for example lateral to the falciform ligament 50. In another example, the magnetic device 10 can be placed along resection line 42*c*, which can extend from the superior side of the right lobe lateral to the vena cava, for example in a right dome 60, to the inferior side of the right lobe of the liver, near the gallbladder, for example medial to an area related to the costodiaphragmatic recess 62 on the anterior side of the liver and a renal impression 64 on the posterior side of the liver.

In such implementations, the magnet assembly 12 can be placed at a desired location around the outer surface of the liver by inserting the resection device 10 in an extended pre-resection configuration in the body cavity and placing it around the outer surface of the liver. The insertion and guiding of the magnet assembly 12 can be done laparoscopically for a minimally invasive procedure, which also advantageously enables minimal disturbance of the connective tissue, arteries, veins and other organs surrounding the liver. When inserting the magnet assembly 12 into the body cavity in the extended pre-resection configuration, the magnet assembly 12 can be navigated around the outer surface of the liver, and aligned with the desired resection line 42*a*, 42*b*, or 42*c*. While resection lines 42*a*, 42*b*, and 42*c* are specifically mentioned here, it should be considered that the magnetic device 10 can be positioned on any resection line for a liver resection, such as for a right hepatectomy, an extended right hepatectomy, a right trisegmentectomy, a right lobectomy, an extended left hepatectomy, or a left trisegmentectomy, for example. Once a proper alignment of the magnet assembly 12 is obtained, the magnet elements 16 of the first zone 38 of the magnet assembly 12 can be brought in sufficiently close proximity of the magnet elements 16 of the second zone 40 of the magnet assembly 12 such that the magnet-engaging sides of the magnet elements 16 of the first zone 38 can be magnetically coupled to the magnet-engaging sides of the magnet elements 16 of the second zone 40. As mentioned above, the attractive force of the magnet elements 16 can be chosen to enable trial and error until proper placement of the magnet assembly 12 is achieved.

Alternatively, placement of the magnet assembly 12 can be performed during an open surgery. In such cases, the magnet assembly 12 can be provided for placement around the liver either in the extended pre-resection configuration or in the looped pre-resection configuration. Multiple other techniques can also be used to position and implant the magnet assembly 12. For instance, image-guided procedures (e.g., ultrasound, magnetic resonance imaging, computed tomography and the like) and flexible endoscopy are techniques that can be used to insert and/or position the magnet assembly 12 adequately around the target solid organ. It is to be noted that any other suitable techniques allowing to insert and/or place the magnet assembly 12 around the outer surface of the target solid organ can also be used, such as robot-assisted surgery.

Figure 25:
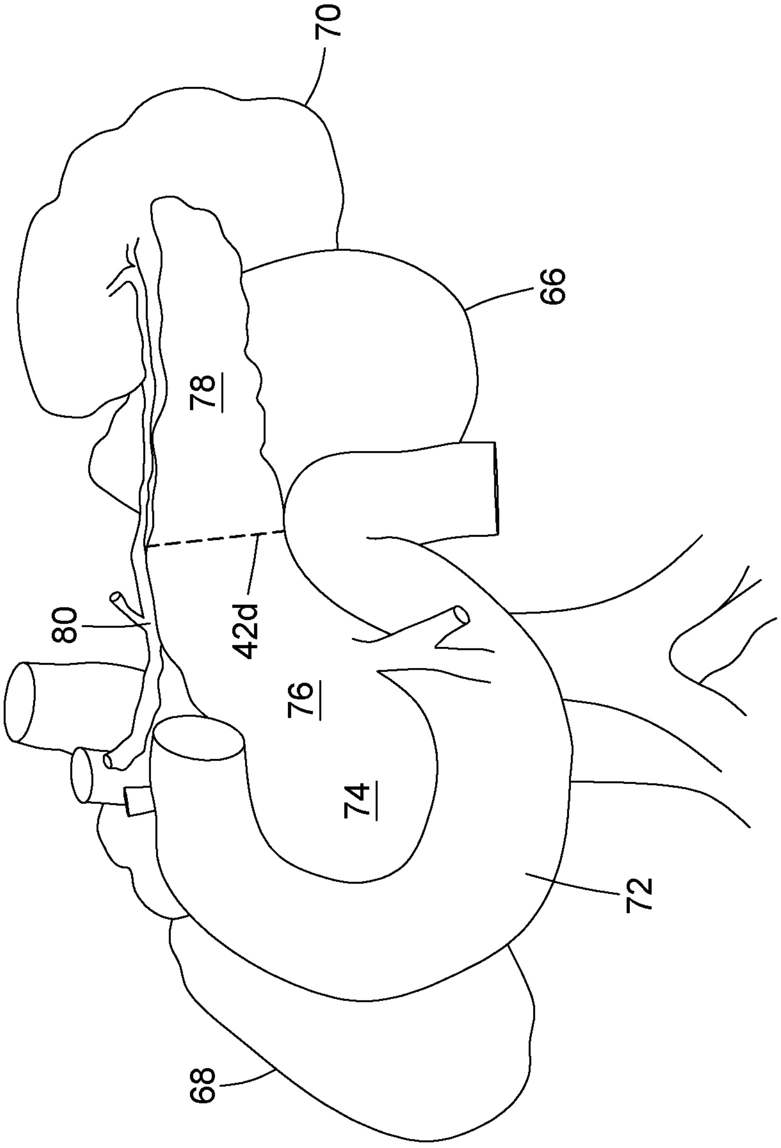
FIG. 25 is an anterior view schematic a pancreas within the body cavity, showing a transverse resection line between the head and the tail of the pancreas.

Referring to FIG. 25, a pancreas 64 in a body cavity with a left kidney 66 and a right kidney 68, spleen 70, and duodenum 72 is shown with a resection line 42*d* in the pancreas for use in a pancreatectomy. In some implementations, the resection line 42*d* can extend substantially vertically between a head 74 or pancreatic neck 76 and a tail 78 of the pancreas. For example, the resection line 42*d* can extend from the superior side of the pancreas near the splenic artery 80 to the inferior side of the pancreas near the duodenum 72. In other implementations, the magnetic device 10 can be position along other resection lines.

Figure 26:
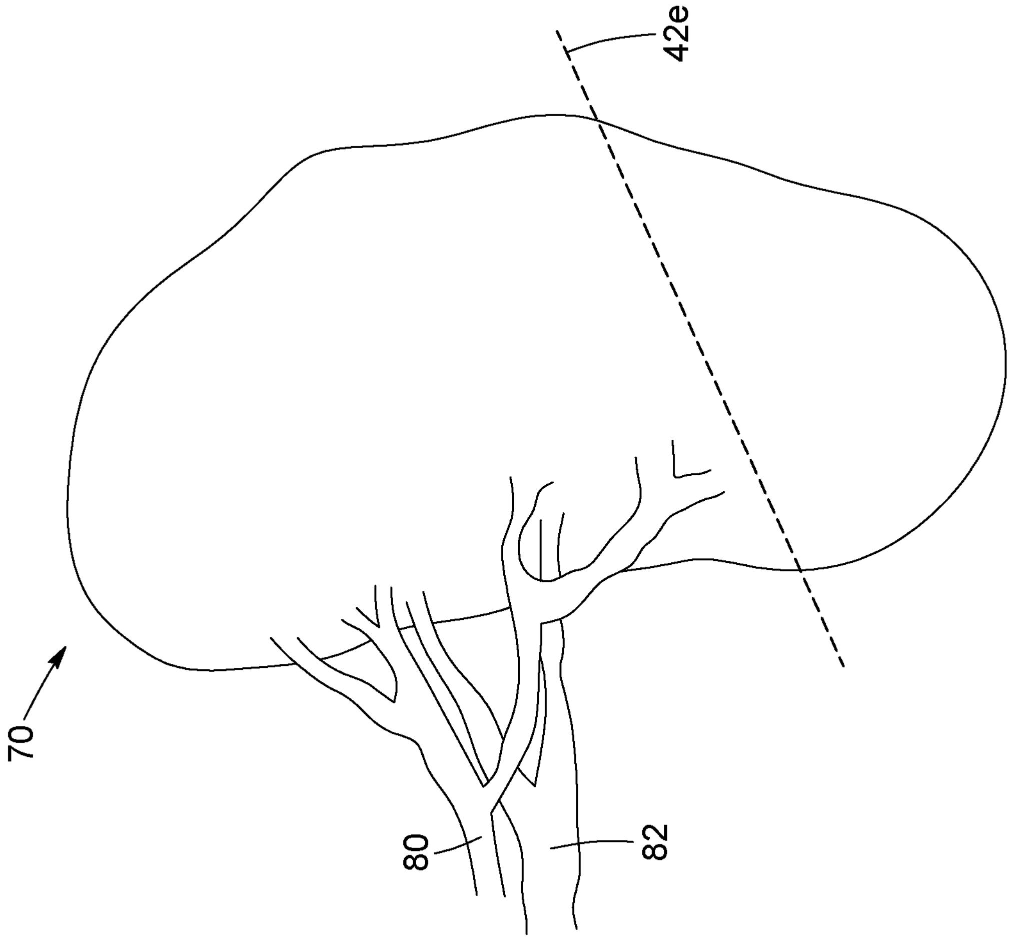
FIG. 26 is an anterior view schematic of a spleen, showing a transverse resection line in a lower region thereof.

With reference to FIG. 26, a spleen 70 with a resection line 42*e* is shown. In some implementations, such as when a portion of the spleen 70 is removed, the resection line 42*e* can extend along an inferior portion of the spleen, for example on a portion that is inferior to the splenic artery 80 and the splenic vein 82, thus providing a resection of the spleen. In other implementations, the magnetic device 10 can be positioned along a resection line that provides for a complete removal of the entire spleen.

Figure 27:
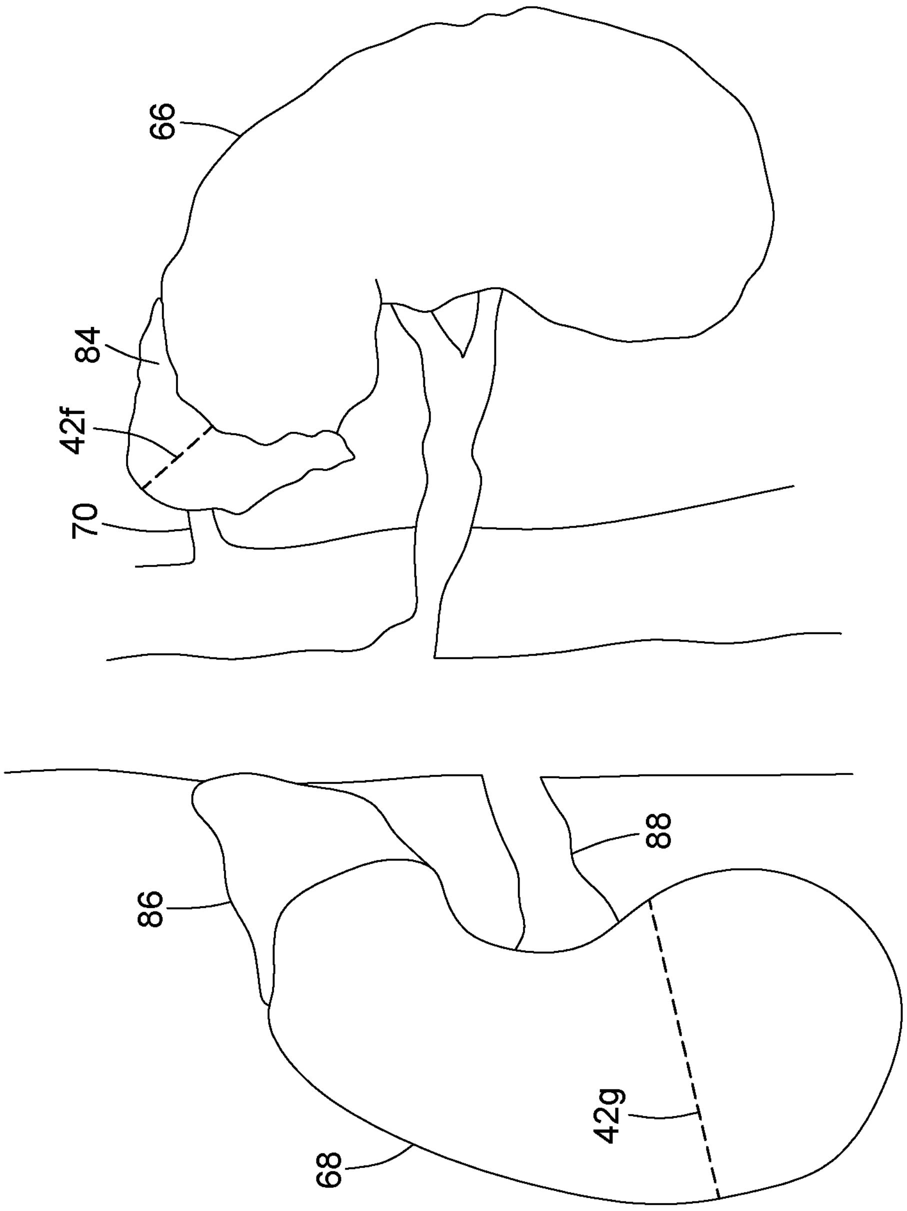
FIG. 27 is an anterior view schematic of a left and a right kidney each connected to a left and a right adrenal gland, respectively, showing a transverse resection line in a lower region of the right kidney and a transverse resection line in a middle region of the left adrenal gland.

FIG. 27 illustrates a portion of a body cavity showing the left kidney 66 and the right kidney 68, each in proximity to a left adrenal gland 84 and a right adrenal gland 86, respectively. An implementation of a resection line 42*f* located on the left adrenal gland is shown. The resection line 42*f* extends from the superior side of the adrenal gland, for example in proximity to the left superior adrenal artery 88, to a lateral side of the adrenal gland that is in proximity of the left kidney 66. In other implementations, the resection line can be located on the right adrenal gland 86.

Still referring to FIG. 27, an implementation of a resection line 42*g* extending transversally across an inferior portion of the right kidney 68 is also shown. In this implementation, the resection line 42*g* extends substantially transversally across the kidney at a position inferior to the renal artery, the renal vein 88 and the ureter. In other implementations, the resection line can be located on the left kidney, in another position on the kidney.

Similarly to what is described above with regard to FIGS. 24A and 24B, the magnet assembly 12 can be placed at a desired location around the outer surface of the pancreas, spleen, adrenal gland, or kidney by inserting the resection device 10 in an extended pre-resection configuration in the body cavity and placing it around the outer surface of the target solid organ. The insertion and guiding of the magnet assembly 12 can be done laparoscopically for a minimally invasive procedure, which also advantageously enables minimal disturbance of the connective tissue, arteries, veins and other organs surrounding the target solid organ. When inserting the magnet assembly 12 into the body cavity in the extended pre-resection configuration, the magnet assembly 12 can be navigated around the outer surface of the target solid organ, and aligned with the desired resection line 42*d*, 42*e*, 42*f*, 42*g*, or another resection line required for the desired outcome.

Figure 28B:
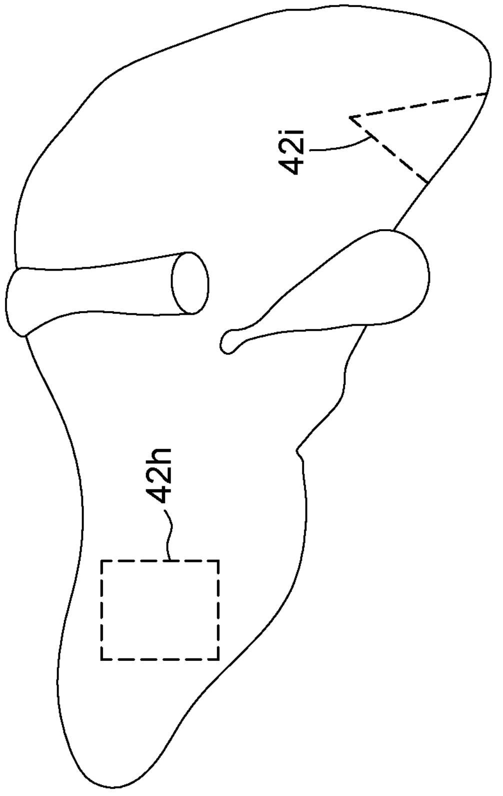
FIG. 28B is a posterior view schematic of a liver, showing an enclosed resection line on an interior region of the liver and a resection line along a periphery region of the liver.
Figure 28A:
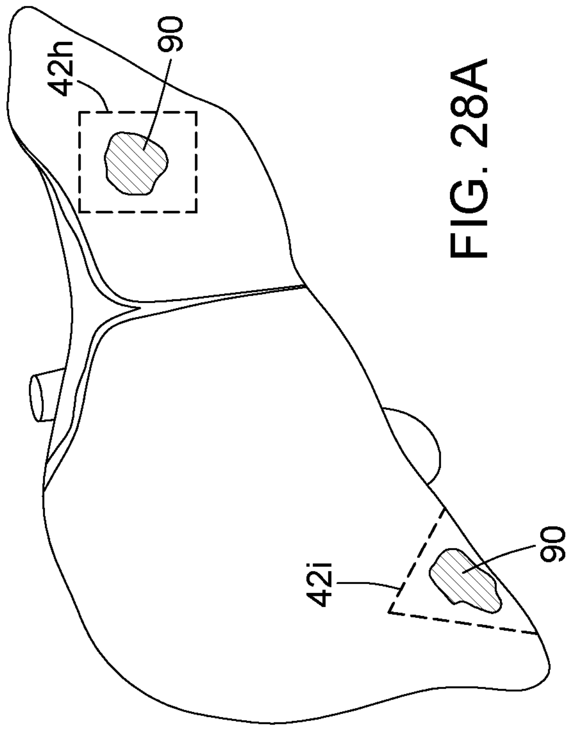
FIG. 28A is an anterior view schematic of a liver, showing an enclosed resection line on an interior region of the liver and a resection line along a periphery region of the liver.

FIGS. 28A and 28B illustrate an anterior view and a posterior view, respectively, of a liver. An example of an enclosed resection line 42*h* in an interior region of the liver is shown. The magnetic device 10 can be positioned along the enclosed resection line 42*h* to facilitate the resection of a portion of the left lobe of the liver, for example to remove a lesion 90. A resection device 10 with a magnetic assembly 12 that includes a first set of magnet elements 16 corresponding to a first zone 38 and a second set of magnet elements 16 corresponding to a second zone 40, each of the first and second sets of magnet elements 16 being provided in an enclosed shape. The first set of magnet elements 16 is positioned along the enclosed resection line 42*h*, on one side of the liver, and the second set of magnet elements 16 is provided on the other side of the liver. In this implementation, the first and second sets of magnet elements 16 forming the first zone 38 and second zone 40 respectively can be connected via a flexible connector 48, or the first and second sets of magnet elements 16 forming the first zone 38 and second zone 40 respectively can be separate from each other. In either implementation, the first zone 38 can be positioned on resection line 42*h* on one side of the organ, in the case of FIG. 28A, the anterior side of the liver, and the second zone 40 can be positioned on resection line 42*h* on an opposing side of the organ, in the case of FIG. 28B, the posterior side of the liver.

Figure 29B:
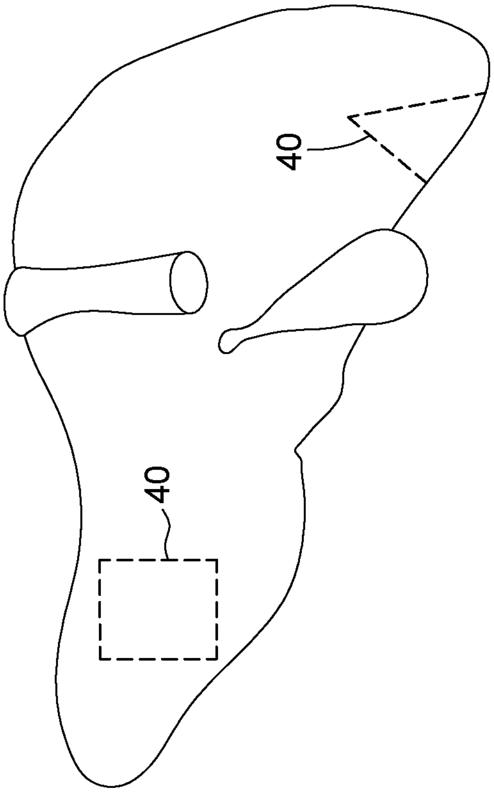
FIG. 29B is an anterior view schematic of a liver, showing two embodiments of a second zone of magnetic elements forming an enclosed shape.
Figure 29A:
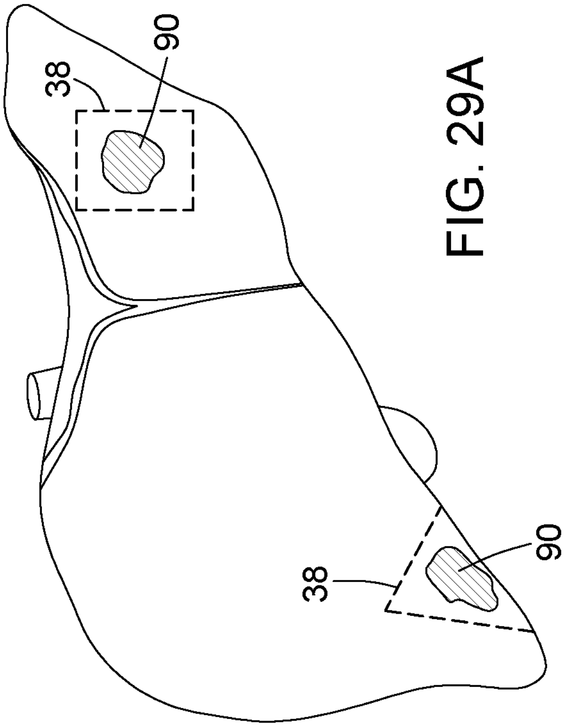
FIG. 29A is an anterior view schematic of a liver, showing two embodiments of a first zone of magnetic elements forming an enclosed shape.

Still referring to FIGS. 28A and 28B, an example of a resection line 42*i* carving out a portion along a periphery region of the liver is shown. The magnetic device 10 can be positioned along the resection line 42*i* to facilitate the removal of a portion of the organ that is in a periphery region of the liver, such as to remove a lesion 90. Specifically, the zones 38, 40 of the magnetic assembly 12 are respectively positioned on opposing sides of the organ, in this case the anterior and posterior sides of the liver, as shown in FIGS. 29A and 29B. The first zone 38 and the second zone 40 can be separate assemblies that are connected with a flexible connector 48. Alternatively, the first zone 38 and the second zone 40 can be part of a single magnet assembly 12 that folds around the periphery of the organ. For example, with a substantially triangular resection line 42*i* when viewed from either the anterior or posterior side of the liver, the magnet elements 16 of the magnetic assembly 12 can be in a continuous formation forming a rhombus, such that when folded around the periphery of the organ, the first zone 38 forms a triangle on one side of the organ, such as the anterior side of the liver, and the second zone 40 forms a triangle on the opposite side of the organ, such as the posterior side of the liver.

It is to be understood that an enclosed resection line in the interior region or a resection line carving out a portion of the organ along a periphery region can be used to position a resection device 10 with magnet elements 16 in a continuous formation forming an enclosed shape on any solid organ, including a kidney, adrenal gland, spleen, or pancreas.

Method for Implanting the Resection Device

A method for removing at least a portion of a solid organ of a patient using a resection device as described herein will now be described in further detail.

The resection device includes a leading elongated member and a trailing elongated member, with a magnet assembly extending therebetween. The magnet assembly includes a plurality of magnet elements flexibly connected in series. The leading elongated member can include any type of flexible member. In some implementations, the leading elongated member can be configured for engagement with a delivery catheter to allow the elongated member to be navigated laparoscopically. In some implementations, the trailing elongated member can also include any type of flexible member that can optionally be configured to be engaged with a delivery catheter or to remain outside the patient or in a subcutaneous location. Alternatively, at least one of the leading elongated member and the trailing elongated member can be omitted.

When the leading elongated member is present, the method can include inserting the leading elongated member and the magnet assembly of the resection device into a body cavity of the patient. As the resection device is an implant that is configured to remain in the body cavity of the patient for a certain period of time, the resection device may be sterilized prior to insertion into the body cavity of the patient. For insertion into the body cavity of the patient, the magnet assembly can be either in an extended pre-resection configuration or in a looped pre-resection configuration. In other implementations, the magnet assembly can form an enclosed shape that can be folded against opposing sides of the target solid organ, or the magnet assembly can include a first and second set of magnet elements each configured to be provided on a corresponding side of the target solid organ. The magnet assembly can be then guided to a target solid organ via the leading elongated member, when present, of the resection device, to position the magnet assembly around a portion of an outer surface of the solid organ such that an anterior portion (or first portion) of the magnet assembly and a posterior portion (or second portion) of the magnet assembly face each other. Various techniques can be used to insert the magnet assembly into the body cavity of the patient and place the magnet assembly around or against the outer surface of the target solid organ. These techniques can include laparoscopic surgery, open surgery, image-guided procedures, flexible endoscopy, and robot-assisted surgery, for instance. When the anterior portion of the magnet assembly faces the posterior portion of the magnet assembly, the magnet-engaging sides of the magnet elements from a first zone of the magnet assembly face the magnet-engaging sides of the magnet elements from a second zone of the magnet assembly while the magnet elements remain magnetically uncoupled in a looped pre-resection configuration to facilitate placement of the magnet assembly along a desired resection line.

Once the magnet elements on both sides of the magnet assembly are aligned as desired along the resection line, the magnet elements can be brought closer together in a resection configuration. In the resection configuration, the magnet elements of the first zone can magnetically couple to at least some of the magnet elements of the second zone or can exert a magnetic attractive force on the outer surface of the target solid organ to compress the target solid organ along the resection line. In other words, magnet elements that are facing each other and that are in sufficiently close proximity can become magnetically coupled to each other via their respective magnet engaging sides to compress the solid organ therebetween, starting with magnet elements at each end of the first zone and the second zone (i.e., the magnet elements near the transition from the first zone to the second zone and the magnet elements at the leading end of the first zone and the trailing ends of the second zone) and progressing toward a central region of the target solid organ until all the magnet elements on either side of the target solid organ are magnetically coupled. Once the magnet elements are magnetically coupled along the resection line and the healing period is completed, the target solid organ can be separated into a resectioned portion and a retained portion. In some implementations, when the magnet elements are received in a housing, the housing includes an organ-contacting side and the opposing outer surfaces of the target solid organ are compressed between the organ-contacting sides of the housing that are facing each other. In some implementations, the organ-contacting side of the housing can be an elongated flat contact surface.

In some implementations, the leading elongated member can be brought in proximity of the trailing elongated member, and one or both of the leading elongated member and the trailing elongated member can be placed outside of the patient or can remain in a sous-cutaneous location. In other implementations, the leading elongated member and the trailing elongated member can be a continuous elongated member that is slidably engaged with the magnet assembly and once the magnet assembly is implanted in the resection configuration, the leading elongated member and the trailing elongated member can be removed from the body cavity of the patient by pulling on one of the leading elongated member and the trailing elongated member.

Following the implantation of the magnet assembly around or against the target solid organ in the resection configuration, the magnet assembly is left implanted for a duration of a healing period of time that is sufficient to facilitate a compression of the solid organ along the resection line to cause ischemic pressure necrosis resulting in a complete resection of a portion of the target solid organ. In other implementations, the compression of the opposing outer surfaces of the target solid organ can cause ischemic pressure necrosis resulting in a partial resection of the resectioned portion (i.e., the resectioned portion and the retained portion are at least partially connected via loose or areolar connective tissue or scar tissue), and the resectioned portion can be fully removed at the same time as the magnetic device is removed by the aid of a cutting tool manipulated by the surgeon. In some implementations, the healing period can extend from between about 1 week and about 6 weeks, in other implementations the healing period can extend from between 10 days to 20 days. In some implementations, monitoring the healing process can be performed to determine at which moment the portions on either side of the resection line of the target solid organ are partially or fully separated from each other, i.e., the resectioned portion is no longer attached to the retained portion of the target solid organ and the retained portion side of the resection line is healed. The duration of the healing period can depend for instance of the target solid organ, the configuration of the magnet assembly, the condition of the patient, and various other factors. In other implementations, the relative position of the first zone and the second zone of the resection device can be monitored externally, such as via X-ray, to determine when all or substantially all the magnet elements have magnetically coupled with their corresponding opposing magnet elements on the corresponding portion (i.e., the magnetic-coupling sides of the first zone and the second zone have magnetically coupled).

Once the resectioned portion is completely or partially separated from retained portion of the target solid organ and healing along the resection line of the target solid organ is partially or entirely completed, the magnet assembly can be removed from the body cavity of the patient. The method for removing the magnet assembly can vary depending on the design of the resection device. In some implementations, a fibrous capsule can form along the magnet elements of the resection device, and the fibrous capsule can be divided or opened, such as by the aid of a cutting tool manipulated by the surgeon, to facilitate the removal of the resection device. In other implementations, such as when a magnet elements forming an enclosed shape are utilized, the resectioned portion can be removed by dividing or opening the fibrous capsule on the anterior and posterior side of the magnet assembly and carving out the resectioned portion of the solid organ within the resection line.

The magnet assembly can be removed from the target solid organ and the body cavity laparoscopically by pulling one of the leading elongated member and the trailing elongated member out of the patient, optionally with a delivery catheter. The magnet assembly can also be removed from the target solid organ and the body cavity laparoscopically by pulling directly the magnet assembly out of the patient, also optionally with a delivery catheter. In some implementations, the magnet assembly can be removed during an open surgery. Again, various techniques can be used to remove the magnet assembly from the body cavity of the patient, which may be the same or different as the technique used previously to insert and place the magnet assembly round the target solid organ, and can include laparoscopic surgery, open surgery, image-guided procedures, flexible endoscopy, and robot-assisted surgery, for instance.

Several alternative implementations and examples have been described and illustrated herein. The implementations of the technology described above are intended to be exemplary only. A person of ordinary skill in the art would appreciate the features of the individual implementations, and the possible combinations and variations of the components. A person of ordinary skill in the art would further appreciate that any of the implementations could be provided in any combination with the other implementations disclosed herein. It is understood that the technology may be embodied in other specific forms without departing from the central characteristics thereof. The present implementations and examples, therefore, are to be considered in all respects as illustrative and not restrictive, and the technology is not to be limited to the details given herein. Accordingly, while the specific implementations have been illustrated and described, numerous modifications come to mind.

The invention claimed is:

1. A resection device to resection a portion of a solid organ in a body cavity of a patient, the resection device comprising:

a magnet assembly implantable into the body cavity of the patient and comprising:

a plurality of magnet elements flexibly connected in series;

wherein the magnet assembly is configured to be positioned against at least a portion of an outer surface of the solid organ to magnetically couple opposing ones of the plurality of magnet elements together to compress opposite sides of the solid organ therebetween along a resection line to subject the solid organ to ischemic pressure necrosis along at least a portion of the resection line to form a resectioned portion and a retained portion over time.

2. The resection device of claim 1, wherein:

each one of the plurality of magnet elements comprises a magnet-engaging side to magnetically couple opposing magnet-engaging sides of the plurality of magnet elements facing each other; and the magnet assembly comprises a first zone and a second zone, the magnet-engaging sides of the magnet elements of the first zone of the magnet assembly having a first zone magnetic pole, and the magnet-engaging sides of the magnet elements of the second zone of the magnet assembly having a second zone magnetic pole that is different from the first zone magnetic pole.

3. The resection device of claim 2, wherein the magnet-engaging side of each of the plurality of magnet elements has a smaller surface area compared to a side of each of the plurality of magnet elements located opposite the magnet-engaging side.

4. The resection device of claim 2, wherein the plurality of magnet elements in the first zone forms a first enclosed shape and the plurality of magnet elements in the second zone forms a second enclosed shape, the first enclosed shape being substantially similar to the second enclosed shape and corresponding to an enclosed shape.

5. The resection device of claim 2, wherein the plurality of magnet elements in the first zone and the plurality of magnet elements in the second zone together form an enclosed shape.

6. The resection device of claim 5, wherein adjacent ones of the plurality of magnet elements forming the enclosed shape are flexibly connected in series to each other via a connector configured to retain the enclosed shape.

7. The resection device of claim 5, wherein the magnet elements of the first zone and the magnet elements of the second zone are each received in a housing defining the enclosed shape.

8. The resection device of claim 1, wherein the magnet elements comprise bevelled edges.

9. The resection device of claim 1, wherein adjacent ones of the plurality of magnet elements are flexibly connected in series via a flexible connector.

10. The resection device of claim 1, wherein the resection device is configurable between a pre-resection configuration and a resection configuration.

11. The resection device of claim 1, wherein the resection device comprises a curved region.

12. The resection device of claim 1, wherein an attractive force of the magnet elements is determined so as to facilitate placement and implantation of the resection device around the portion of the outer surface of the solid organ.

13. The partitioning device of claim 1, wherein the plurality of magnet elements flexibly connected in series are provided in sufficiently close proximity to enable formation of a substantially continuous resection line.

14. The resection device of claim 1, wherein the plurality of magnet elements is received in a housing.

15. The resection device of claim 14, wherein the housing comprises bevelled edges.

16. The resection device of claim 1, wherein each magnet element of the plurality of magnet elements is received in a corresponding housing.

17. The resection device of claim 16, wherein the corresponding housing comprises bevelled edges.

18. A resection device to resection a portion of a solid organ of a patient, the resection device comprising:

a leading elongated member and a trailing elongated member; and a magnet assembly extending between the leading elongated member and the trailing elongated member, the magnet assembly being implantable into a body cavity of the patient and comprising:

a plurality of magnet elements flexibly connected in series;

wherein the magnet assembly is configured to be positioned around a portion of an outer surface of the solid organ by guiding the leading elongated member of the resection device to magnetically couple opposing ones of plurality of magnet elements together to compress the solid organ therebetween along a resection line to subject the solid organ to ischemic pressure necrosis along at least a portion of the resection line to form a resectioned portion and a retained portion over time.

19. The resection device of claim 18, wherein at least one of the leading elongated member and the trailing elongated member is configured to anchor the resection device subcutaneously or outside the patient while opposite sides of the solid organ are compressed between the opposing ones of the plurality of magnet elements.

20. The resection device of claim 18, wherein the leading elongated member and the trailing elongated member comprise a continuous elongated member configured to be slidably engageable with the magnet assembly.

* * * * *